(12) United States Patent
Yamaguchi et al.

(10) Patent No.: US 9,175,073 B2
(45) Date of Patent: Nov. 3, 2015

(54) METHODS FOR DETECTING TH1 CELLS

(71) Applicant: Eisai R&D Management Co., Ltd., Tokyo (JP)

(72) Inventors: Keiko Yamaguchi, Kyoto (JP); Toshio Imai, Kyoto (JP); Kenzo Muramoto, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 37 days.

(21) Appl. No.: 13/840,927

(22) Filed: Mar. 15, 2013

(65) Prior Publication Data

US 2013/0230523 A1  Sep. 5, 2013

Related U.S. Application Data

(62) Division of application No. 13/207,837, filed on Aug. 11, 2011, which is a division of application No. 11/568,435, filed as application No. PCT/JP2005/008150 on Apr. 28, 2005, now Pat. No. 8,017,344.

(30) Foreign Application Priority Data

Apr. 28, 2004 (JP) .................. 2004-133093

(51) Int. Cl.
C07K 16/00 (2006.01)
C07K 16/46 (2006.01)
C07K 16/24 (2006.01)
C07K 16/18 (2006.01)
C07K 16/28 (2006.01)
G01N 33/569 (2006.01)

(52) U.S. Cl.
CPC ............ C07K 16/18 (2013.01); C07K 16/2803 (2013.01); G01N 33/56972 (2013.01); C07K 2316/96 (2013.01); C07K 2317/24 (2013.01); C07K 2317/569 (2013.01); C07K 2317/76 (2013.01); G01N 2333/075 (2013.01); G01N 2333/085 (2013.01)

(58) Field of Classification Search
None
See application file for complete search history.

(56) References Cited

U.S. PATENT DOCUMENTS

| 5,843,712 | A | 12/1998 | Levine |
| 6,613,580 | B1 | 9/2003 | Chow |
| 7,041,804 | B2 * | 5/2006 | Desnoyers et al. ........ 530/387.9 |
| 2003/0092888 | A1 | 5/2003 | Baker |
| 2003/0130182 | A1 | 7/2003 | Ashkenazi |
| 2003/0134352 | A1 | 7/2003 | Freimuth et al. |
| 2007/0021597 | A1 | 1/2007 | Edwards |
| 2011/0294986 | A1 | 12/2011 | Yamaguchi et al. |
| 2013/0231466 | A1 | 9/2013 | Yamaguchi et al. |
| 2014/0242068 | A1 * | 8/2014 | Parkos et al. ............. 424/131.1 |
| 2015/0056201 | A1 | 2/2015 | Yamaguchi et al. |

FOREIGN PATENT DOCUMENTS

WO    WO 98/33819    8/1998
WO    WO 03/082891   10/2003

OTHER PUBLICATIONS

Zen et al. Neutrophil Migration across Tight Junctions is Mediated by Adhesive Interactions between Epithelial Coxsackie and Adenovirus Receptor and a Junctional Adhesion Molecule-like Protein on Neutrophils. Mol Biol Cell. Jun. 2005; 16(6): 2694-2703.*
Zen et al. Neutrophil migration across epithelial tight junctions is regulated by binding interactions between JAML and CAR. FASEB Journal, (Mar. 7, 2005) vol. 19, No. 5, Suppl. S, Part 2, pp. A1526.*
Bhaskar et al. A function blocking anti-mouse integrin α5β1 antibody inhibits angiogenesis and impedes tumor growth in vivo. Journal of Translational Medicine 2007, 5:61.*
Moog-Lutz et al. JAML, a novel protein with characteristics of a junctional adhesion molecule, is induced during differentiation of myeloid leukemia cells. Blood 102 (9): 3371-8.*
Amendment and Argument in Reply to Office Action dated Jul. 15, 2010, issued for Japanese Application No. 2006-512835, 56 pages.
Attwood, "Genomics. The Babel of bioinformatics," *Science*, 2000, 290(5491):471-473.
Bergelson et al, "The murine CAR homolog is a receptor for coxsackie B viruses and adenovirus," *Journal of Virology*, Jan. 1988; pp. 415-419, 72:1.
Bergelson et al., "Isolation of a common receptor for Coxsackie B viruses and adenoviruses 2 and 5," *Science*, Feb. 28, 1997, pp. 1320-1323.
Bowie et al., "Deciphering the message in protein sequences: tolerance to amino acid substitutions," *Science*, 1990, vol. 247, pp. 1306-1310.

(Continued)

*Primary Examiner* — Maher Haddad
(74) *Attorney, Agent, or Firm* — Fish & Richardson P.C.

(57) ABSTRACT

The inventors discovered that the adhesion molecule CAR, known to be localized in intracellular adhesion sites, functioned as an adhesion molecule for activated lymphocytes. Further, the inventors identified CARL, a novel CAR ligand expressed in lymphocytes, and clarified that the ligand was expressed selectively in Th1 cells. In addition, they found that anti-CAR antibodies could inhibit the adhesion of activated lymphocytes to CAR molecules. Thus, the present invention provides methods for detecting Th1 cells using CAR or anti-CARL antibodies, and methods of screening for inhibitors suppressing the adhesion of Th1 cells using the binding between CAR and CARL as an index. Furthermore, the present invention relates to methods of screening for inhibitors of the binding between CAR and CARL, antibodies that inhibit the binding between CAR and CARL, and therapeutic compositions comprising these antibodies. These are expected to be useful in diagnosing diseases, such as inflammation, in which infiltration of Th1 cells is involved, and in providing pharmaceutical agents for alleviating such diseases.

12 Claims, 16 Drawing Sheets

(56) References Cited

OTHER PUBLICATIONS

Cohen et al., "The coxsackievirus and adenovirus receptor is a transmembrane component of the tight junction;" *PNAS: Proceedings of the National Academy of Sciences of the United States of America*; Dec. 18, 2001, pp. 15191-15196; 98:26.
GenBank Accession No. AY358362.1, Oct. 3, 2003, 2 pages.
GenBank Accession No. AK009049.1, Oct. 6, 2010, 4 pages.
GenBank Accession No. Q86YT9, Aug. 10, 2010, pp. 1-4.
Guo et al. "Role of junctional adhesion molecule-like protein in mediating monocyte transendothelial migration," *Arterioscler Thromb Vasc Biol*, 2009, 29(1):75-83.
International Search Report issued for PCT/JP2005/008150, dated Jul. 12, 2005, 1 page.
Kuntz.,"Structure-based strategies for drug design and discovery," *Science*, 1992 257(5073):1078-1082.
Miller et al., "Ligand binding to proteins: the binding landscape model," *Protein Sci*. 1997, 6(10):2166-79.
Moog-lutz et al., "JAML, a novel protein with characteristics of a junctional adhesion molecule, is induced during differentiation of myeloid leukemia cells," *Blood*, Nov. 1, 2003; pp. 3371-3378, 102:9.
Office Action dated Jul. 15, 2010, issued for Japanese Application No. JP2006-512835, 7 pages.
Pickles et al., "Retargeting the Coxsackievirus and Adenovirus Receptor to the Apical Surface of Polarized Epithelial Cells Reveals the Glycocalyx as a Barrier to Adenovirus-Mediated Gene Transfer," *Journal of Virology*, 2000, pp. 6050-6057.
Skolnick et al., "From genes to protein structure and function: novel applications of computational approaches in the genomic era," *Trends Biotechnol.*, 18(1):34-9, 2000.
Strausberg et al., "Mammalian Gene Collection (MSG) Program Team: Generation and initial analysis of more than 15,000 full-length human and mouse cDNA sequences," *PNAS: Proceedings of the National Academy of Sciences of the United States of America*, Dec. 24, 2002; pp. 16899-16903, 99:26.
Verdino et al. "The molecular interaction of CAR and JAML recruits the central cell signal transducer PI3K". *Science*, 2010, 329:1210-14.
Walters et al., "Adenovirus Fiber Disrupts CAR-Mediated Intercellular Adhesion Allowing Virus Escape," *Cell*, Sep. 20, 2002, pp. 789-799,110:6.
Wan et al., "Transgenic expression of the coxsackie/adenovirus receptor enables adenoviral-mediated gene delivery in naive T cells," *PNAS*, 2000, vol. 97(25)13784-13789.
Zen et al., "Neutrophil migration across epithelial tight junctions is regulated by binding interactions between JAML and CAR," *FASEB Journal*, Mar. 7, 2005, 19(5): Suppl. S, Part 2, p. A 1526.
Zen et al., "Neutrophil Migration across Tight Junctions is Mediated by Adhesive Interactions between Epithelial Coxsackie and Adenovirus Receptor and a Junctional Adhesion Molecule-like Protein and Neutrophils," *Molecular Biology of the Cell*, Jun. 2005, pp. 2694-2703, 16:6.
Carson et al., "Monoclonal Antibody against Mouse CAR following Genetic Immunization," *Hybridoma and Hybridomics* (2004), 23(1):19-22.
Dmitriev et al., "Ectodomain of Coxsackievirus and Adenovirus Receptor Genetically Fused to Epidermal Growth Factor Mediates Adenovirus Targeting to Epidermal Growth Factor Receptor-Positive Cells," *J. Virology* (2000), 74(15):6875-6884.
Honda et al., "The coxsackievirus-adenovirus receptor protein as a cell adhesion molecule in the developing mouse brain," *Brain Res. Mol. Brain Res.* (2000), 77(1):19-28.
Owens et al., "The genetic engineering of monoclonal antibodies," *J Immunol. Methods* (1994), 168(2):149-165.
Restriction Requirement issued in U.S. Appl. No. 13/207,837, dated Jun. 28, 2012, 4 pages.
Response to Restriction Requirement filed Aug. 27, 2012 in U.S. Appl. No. 13/207,837, 4 pages.
Office Action issued in U.S. Appl. No. 13/207,837, dated Sep. 21, 2012, 15 pages.
Response to Office Action filed Feb. 21, 2013 in U.S. Appl. No. 13/207,837, 14 pages.
Office Action issued in U.S. Appl. No. 13/207,837, dated Sep. 25, 2013, 19 pages.
Office Action issued in U.S. Appl. No. 13/207,837, dated Mar. 25, 2013, 20 pages.
D'Andrea et al , "Inhibition of Receptor Binding and Neutralization of Bioactivity by Anti-Erythropoietin Monoclonal Antibodies," *Blood*, Feb. 15, 1990, 75(4):874-880.
Karpusas et al., "Structure of CD40 Ligand in Complex with the Fab Fragment of a Neutralizing Humanized Antibody," *Structure*, Apr. 2001, 9:321-329.
Kubo et al., "Neutralization and fusion inhibition activities of monoclonal antibodies specific for the S1 subunit of the spike protein of neurovirulent murine coronavirus JHMV c1-2 variant," *J Gen Virol.*, 1993, 74, 1421-1425.
Kubo et al., "Localization of Neutralizing Epitopes and the Receptor-Binding Site within the Amino-Terminal 330 Amino Acids of the Murine Coronavirus Spike Protein," *J Virol.*, Sep. 1994, 68(9):5403-5410.
Tahara et al., "Neutralization of Biological Activity and Inhibition of Receptor Binding by Antibodies Against Human Thrombopoietin," *Stem Cells*, 1998, 16:54-60.
Takemoto et al., "Anti-Human IgE Monoclonal Antibodies Recognizing Epitopes Related to the Binding Sites of High and Low Affinity IgE Receptors," *Microbiol. Immunol.*, 1994, 38(1):63-71.
Office Action issued in U.S. Appl. No. 13/840,851, dated Oct. 9, 2014, 20 pages.
Tomko et al., "HCAR and MCAR: The human and mouse cellular receptors for subgroup C adenoviruses and group B coxsackieviruses," *Proc. Natl. Acad. Sci. USA* (1997); 94(7):3352-3356.
Office Action issued in U.S. Appl. No. 13/207,837, dated Apr. 17, 2014, 15 pages.
GenBank: AAM15732.1. Dendtritic-cell specific protein Crea7 [Mus musclus]. Mar. 4, 2005, pp. 1-2.
Office Action issued in U.S. Appl. No. 13/207,837 dated Apr. 17, 2014, 15 pages.
Office Action issued in U.S. Appl. No. 13/840,851, dated Feb. 17, 2015, 10 pages.
Request for Continued Examination (RCE), Amendment after Final, and Rule 132 Declaration for U.S. Appl. No. 13/207,837.
Response to Office Action filed Jan. 9, 2015 in U.S. Appl. No. 13/840,851, 9 pages.
Tomko et al. HCAR and MCAR: The human and mouse cellular receptors for subgroup C adenoviruses and group B coxsackieviruses. Proc Natl Acad Sci USA. Apr. 1, 1997; 94(7): 3352-3356.
Response to Office Action filed May 13, 2015 in U.S. Appl. No. 13/840,851, 6 pages.
Office Action issued in U.S. Appl. No. 13/840,851, dated Jun. 3, 2015, 6 pages.
Response to Office Action and Request for Continued Examination filed in U.S. Appl. No. 13/840,851, filed Aug. 31, 2015, 9 pages.

* cited by examiner

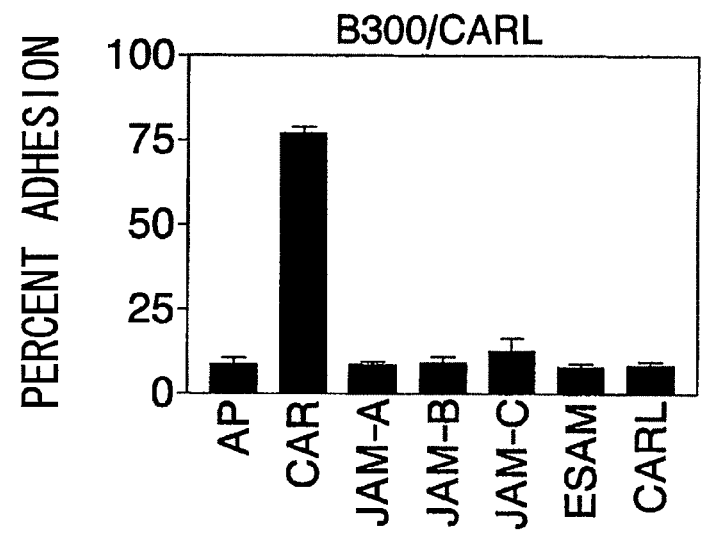
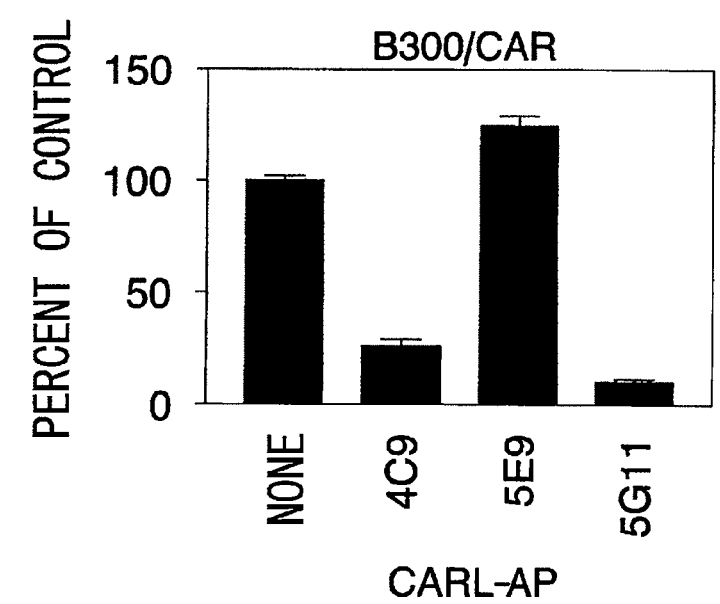
FIG. 6

|     |                                          |     |
| --- | ---------------------------------------- | --- |
|   1 | MLCLLKLIVIPVILAPVGYPQGLPGLTVSS           |  30 |
|  31 | PQLRVHVGESVLMGCVVQRTEEKHVDRVDW           |  60 |
|  61 | LFSKDKDDASEYVLFYYSNLSVPTGRFQNR           |  90 |
|  91 | SHLVGDTFHNDGSLLLQDVQKADEGIYTCE           | 120 |
| 121 | IRLKNESMVMKKPVELWVLPEEPKDLRVRV           | 150 |
| 151 | GDTTQMRCSIQSTEEKRVTKVNWMFSSGSH           | 180 |
| 181 | TEEETVLSYDSNMRSGKFQSLGRFRNRVDL           | 210 |
| 211 | TGDISRNDGSIKLQTVKESDRGIYTCSIYV           | 240 |
| 241 | GKLESRKTIVLHVVQDEFQRTISPTPPTDK           | 270 |
| 271 | GQQGILNGNQLVIIVGIVCATFLLLPVLIL           | 300 |
| 301 | IVKKAKWNKSSVSSMASVKSLENKEKINPE           | 330 |
| 331 | KHIYSSITTWETTERGISGESEGTYMTMNP           | 360 |
| 361 | VWPSSPKASSLVRSSVRSK (SEQ ID NO: 1)       | 379 |

FIG. 7

SEQUENCE LISTING

<160> NUMBER OF SEQ ID NOS: 19

<210> SEQ ID NO 1
<211> LENGTH: 379
<212> TYPE: PRT
<213> ORGANISM: Mus musculus
<220> FEATURE:
<223> OTHER INFORMATION: mouse Coxackie virus and Adenovirus receptor
      ligand (CARL)

<400> SEQUENCE: 1

Met Leu Cys Leu Leu Lys Leu Ile Val Ile Pro Val Ile Leu Ala Pro
 1               5                  10                  15

Val Gly Tyr Pro Gln Gly Leu Pro Gly Leu Thr Val Ser Ser Pro Gln
            20                  25                  30

Leu Arg Val His Val Gly Glu Ser Val Leu Met Gly Cys Val Val Gln
        35                  40                  45

```
Arg Thr Glu Glu Lys His Val Asp Arg Val Asp Trp Leu Phe Ser Lys
 50                  55                  60

Asp Lys Asp Asp Ala Ser Glu Tyr Val Leu Phe Tyr Tyr Ser Asn Leu
 65                  70                  75                  80

Ser Val Pro Thr Gly Arg Phe Gln Asn Arg Ser His Leu Val Gly Asp
                 85                  90                  95

Thr Phe His Asn Asp Gly Ser Leu Leu Leu Gln Asp Val Gln Lys Ala
                100                 105                 110

Asp Glu Gly Ile Tyr Thr Cys Glu Ile Arg Leu Lys Asn Glu Ser Met
            115                 120                 125

Val Met Lys Lys Pro Val Glu Leu Trp Val Leu Pro Glu Glu Pro Lys
130                 135                 140

Asp Leu Arg Val Arg Val Gly Asp Thr Thr Gln Met Arg Cys Ser Ile
145                 150                 155                 160

Gln Ser Thr Glu Glu Lys Arg Val Thr Lys Val Asn Trp Met Phe Ser
                165                 170                 175

Ser Gly Ser His Thr Glu Glu Glu Thr Val Leu Ser Tyr Asp Ser Asn
                180                 185                 190

Met Arg Ser Gly Lys Phe Gln Ser Leu Gly Arg Phe Arg Asn Arg Val
            195                 200                 205

Asp Leu Thr Gly Asp Ile Ser Arg Asn Asp Gly Ser Ile Lys Leu Gln
210                 215                 220

Thr Val Lys Glu Ser Asp Arg Gly Ile Tyr Thr Cys Ser Ile Tyr Val
225                 230                 235                 240

Gly Lys Leu Glu Ser Arg Lys Thr Ile Val Leu His Val Val Gln Asp
                245                 250                 255

Glu Phe Gln Arg Thr Ile Ser Pro Thr Pro Thr Asp Lys Gly Gln
            260                 265                 270

Gln Gly Ile Leu Asn Gly Asn Gln Leu Val Ile Ile Val Gly Ile Val
            275                 280                 285

Cys Ala Thr Phe Leu Leu Leu Pro Val Leu Ile Leu Ile Val Lys Lys
290                 295                 300

Ala Lys Trp Asn Lys Ser Ser Val Ser Ser Met Ala Ser Val Lys Ser
305                 310                 315                 320

Leu Glu Asn Lys Glu Lys Ile Asn Pro Glu Lys His Ile Tyr Ser Ser
                325                 330                 335

Ile Thr Thr Trp Glu Thr Thr Glu Arg Gly Ile Ser Gly Glu Ser Glu
                340                 345                 350

Gly Thr Tyr Met Thr Met Asn Pro Val Trp Pro Ser Ser Pro Lys Ala
            355                 360                 365

Ser Ser Leu Val Arg Ser Ser Val Arg Ser Lys
370                 375

<210> SEQ ID NO 2
<211> LENGTH: 394
<212> TYPE: PRT
<213> ORGANISM: Homo sapiens
<220> FEATURE:
<223> OTHER INFORMATION: human Coxackie virus and Adenovirus receptor
      ligand (CARL)

<400> SEQUENCE: 2

Met Phe Cys Pro Leu Lys Leu Ile Leu Leu Pro Val Leu Leu Asp Tyr
 1               5                  10                  15

Ser Leu Gly Leu Asn Asp Leu Asn Val Ser Pro Pro Glu Leu Thr Val
                20                  25                  30
```

His Val Gly Asp Ser Ala Leu Met Gly Cys Val Phe Gln Ser Thr Glu
 35                  40                  45

Asp Lys Cys Ile Phe Lys Ile Asp Trp Thr Leu Ser Pro Gly Glu His
 50                  55                  60

Ala Lys Asp Glu Tyr Val Leu Tyr Tyr Ser Asn Leu Ser Val Pro
 65              70                  75                  80

Ile Gly Arg Phe Gln Asn Arg Val His Leu Met Gly Asp Ile Leu Cys
                 85                  90                  95

Asn Asp Gly Ser Leu Leu Leu Gln Asp Val Gln Glu Ala Asp Gln Gly
                100                 105                 110

Thr Tyr Ile Cys Glu Ile Arg Leu Lys Gly Glu Ser Gln Val Phe Lys
                115                 120                 125

Lys Ala Val Val Leu His Val Leu Pro Glu Glu Pro Lys Glu Leu Met
130                 135                 140

Val His Val Gly Gly Leu Ile Gln Met Gly Cys Val Phe Gln Ser Thr
145                 150                 155                 160

Glu Val Lys His Val Thr Lys Val Glu Trp Ile Phe Ser Gly Arg Arg
                165                 170                 175

Ala Lys Glu Glu Ile Val Phe Arg Tyr Tyr His Lys Leu Arg Met Ser
                180                 185                 190

Val Glu Tyr Ser Gln Ser Trp Gly His Phe Gln Asn Arg Val Asn Leu
                195                 200                 205

Val Gly Asp Ile Phe Arg Asn Asp Gly Ser Ile Met Leu Gln Gly Val
                210                 215                 220

Arg Glu Ser Asp Gly Gly Asn Tyr Thr Cys Ser Ile His Leu Gly Asn
225                 230                 235                 240

Leu Val Phe Lys Lys Thr Ile Val Leu His Val Ser Pro Glu Glu Pro
                245                 250                 255

Arg Thr Leu Val Thr Pro Ala Ala Leu Arg Pro Leu Val Leu Gly Gly
                260                 265                 270

Asn Gln Leu Val Ile Ile Val Gly Ile Val Cys Ala Thr Ile Leu Leu
                275                 280                 285

Leu Pro Val Leu Ile Leu Ile Val Lys Lys Thr Cys Gly Asn Lys Ser
290                 295                 300

Ser Val Asn Ser Thr Val Leu Val Lys Asn Thr Lys Thr Asn Pro
305                 310                 315                 320

Glu Ile Lys Glu Lys Pro Cys His Phe Glu Arg Cys Glu Gly Glu Lys
                325                 330                 335

His Ile Tyr Ser Pro Ile Ile Val Arg Glu Val Ile Glu Glu Glu
                340                 345                 350

Pro Ser Glu Lys Ser Glu Ala Thr Tyr Met Thr Met His Pro Val Trp
                355                 360                 365

Pro Ser Leu Arg Ser Asp Arg Asn Asn Ser Leu Glu Lys Lys Ser Gly
                370                 375                 380

Gly Gly Met Pro Lys Thr Gln Gln Ala Phe
385                 390

<210> SEQ ID NO 3
<211> LENGTH: 1284
<212> TYPE: DNA
<213> ORGANISM: Mus musculus
<220> FEATURE:
<223> OTHER INFORMATION: mouse Coxackie virus and Adenovirus receptor
      ligand (CARL) cDNA

```
<400> SEQUENCE: 3
cccagacaga atctggctca cattggcact cactgttagt ttgttcagtt aacagtgttc      60
tctggatata attttctgat ttcttttta atcttaagat tgaaaacttg aaaggataat     120
gctttgcctc ctgaaactga ttgtgattcc agtaatcctg gccctgtag gttatccaca     180 gggcctgcca ggcttgaccg tttcctcccc tcagctgaga gtgcatgtgg gtgaatcagt     240
cttgatggga tgtgttgtcc agcgcacaga agagaaacac gtggacagag tggattggct     300
cttctcgaaa gataaagatg atgcgagtga atatgtgctg ttctactatt ccaaccttag     360
cgtgcctacg gggcgcttcc agaaccggtc acatttggtg ggggacacct tccataatga     420
tggttctctc ctgctccaag atgttcagaa ggccgatgag ggaatctaca cctgtgaaat     480
ccgcctcaaa aatgagagca tggtgatgaa aaagcccgtg gaactgtggg tgctaccaga     540
ggaacctaaa gatctcagag tccgagtagg tgatacaact cagatgagat gttctatcca     600
gagcacagaa gagaaacggg tgaccaaagt aaactggatg ttttcttcag ggagccatac     660
tgaggaggag acagtcttga gctatgactc caacatgcgt agtggaaaat ccagagcct     720 gggccgcttc cgcaaccgtg tagacctgac aggtgacatc tcccgcaatg atggctcaat     780
caaacttcaa acagtgaagg agtctgaccg aggaatctac acttgcagca tctacgtggg     840
aaagctggag tccaggaaaa ccattgtgct gcatgtggtc caggacgaat tcaaaggac     900 aatttcacca actcctccaa ctgataaggg tcagcagggc atcctgaatg gaaatcagct     960
ggtgatcatt gtggggatcg tctgtgccac cttcctgctg cttccggttt tgatattaat    1020
tgtgaagaaa gccaagtgga ataagagctc agtaagttct atggcttctg tgaagagcct    1080
ggagaacaaa gagaagatta tccagagaa gcatatctac tcctccataa ctacgtggga    1140
gacgacagag agaggaataa gtggagagtc agagggcacc tacatgacca tgaatccagt    1200
ttggccttct tcccccaaag catccagttt ggtccgctct tcagtcagat ccaagtaatg    1260
tggttgaaaa aaaaaaaaaa aaaa                                          1284

<210> SEQ ID NO 4
<211> LENGTH: 1635
<212> TYPE: DNA
<213> ORGANISM: Homo sapiens
<220> FEATURE:
<223> OTHER INFORMATION: human Coxackie virus and Adenovirus receptor
      ligand (CARL) cDNA

<400> SEQUENCE: 4
tgcagctgtg gggagatttc agtgcattgc ctcccctggg tgctcttcat cttggatttg      60
aaagttgaga gcagcatgtt ttgcccactg aaactcatcc tgctgccagt gttactggat     120
tattccttgg gcctgaatga cttgaatgtt tccccgcctg agctaacagt ccatgtgggt     180
gattcagctc tgatgggatg tgtttttcag agcacagaag acaaatgtat attcaagata     240
gactggactc tgtcaccagg agagcacgcc aaggacgaat atgtgctata ctattactcc     300
aatctcagtg tgcctattgg gcgcttccag aaccgcgtac acttgatggg ggacatctta     360
tgcaatgatg gctctctcct gctccaagat gtgcaagagg ctgaccaggg aacctatatc     420
tgtgaaatcc gcctcaaagg ggagagccag gtgttcaaga aggcggtggt actgcatgtg     480
cttccagagg agcccaaaga gctcatggtc catgtgggtg gattgattca gatgggatgt     540
gttttccaga gcacagaagt gaaacacgtg accaaggtag aatggatatt ttcaggacgg     600
cgcgcaaagg aggagattgt atttcgttac taccacaaac tcaggatgtc tgtggagtac     660
```

```
tcccagagct ggggccactt ccagaatcgt gtgaacctgg tgggggacat tttccgcaat      720
gacggttcca tcatgcttca aggagtgagg gagtcagatg gaggaaacta cacctgcagt      780
atccacctag ggaacctggt gttcaagaaa accattgtgc tgcatgtcag cccggaagag      840
cctcgaacac tggtgacccc ggcagccctg aggcctctgg tcttgggtgg taatcagttg      900
gtgatcattg tgggaattgt ctgtgccaca atcctgctgc tccctgttct gatattgatc      960
gtgaagaaga cctgtggaaa taagagttca gtgaattcta cagtcttggt gaagaacacg     1020
aagaagacta atccagagat aaaagaaaaa ccctgccatt ttgaaagatg tgaaggggag     1080
aaacacattt actccccaat aattgtacgg gaggtgatcg aggaagaaga accaagtgaa     1140
aaatcagagg ccacctacat gaccatgcac ccagtttggc cttctctgag gtcagatcgg     1200
aacaactcac ttgaaaaaaa gtcaggtggg ggaatgccaa aaacacagca agcctttgta     1260
gaagaatgga gagtcccttc atctcagcag cggtggagac tctctcctgt gtgtgtcctg     1320
ggccactcta ccagtgattt cagactcccg ctctcccagc tgtcctcctg tctcattgtt     1380
tggtcaatac actgaagatg gagaatttgg agcctggcag agagactgga cagctctgga     1440
ggaacaggcc tgctgagggg aggggagcat ggacttggcc tctggagtgg gacactggcc     1500
ctgggaacca ggctgagctg agtggcctca accccccgt tggatcagac cctcctgtgg     1560
gcagggttct tagtggatga gttactggga agaatcagag ataaaaacca acccaaatca     1620
aaaaaaaaaa aaaaa                                                     1635

<210> SEQ ID NO 5
<211> LENGTH: 41
<212> TYPE: DNA
<213> ORGANISM: Artificial Sequence
<220> FEATURE:
<223> OTHER INFORMATION: synthetic PCR amplification primer mCAR F1

<400> SEQUENCE: 5
gcggtcgacg ccaccatggc gcgcctactg tgcttcgtgc t                          41

<210> SEQ ID NO 6
<211> LENGTH: 38
<212> TYPE: DNA
<213> ORGANISM: Artificial Sequence
<220> FEATURE:
<223> OTHER INFORMATION: synthetic PCR amplification primer mCAR R2

<400> SEQUENCE: 6
cgccgcggcc gcttatacca ctgtaatgcc atcggtct                              38

<210> SEQ ID NO 7
<211> LENGTH: 38
<212> TYPE: DNA
<213> ORGANISM: Artificial Sequence
<220> FEATURE:
<223> OTHER INFORMATION: synthetic PCR amplification primer mCAR R1

<400> SEQUENCE: 7
cgccgcggcc gctcggttgg agggtgggac aacgtcta                              38

<210> SEQ ID NO 8
<211> LENGTH: 42
<212> TYPE: DNA
<213> ORGANISM: Artificial Sequence
<220> FEATURE:
<223> OTHER INFORMATION: synthetic PCR amplification primer mCARL F1
```

<400> SEQUENCE: 8
gcggtcgacg ccaccatgct ttgcctcctg aaactgattg tg          42

<210> SEQ ID NO 9
<211> LENGTH: 39
<212> TYPE: DNA
<213> ORGANISM: Artificial Sequence
<220> FEATURE:
<223> OTHER INFORMATION: synthetic PCR amplification primer mCARL R2

<400> SEQUENCE: 9
cgcggcggcc gcttacttgg atctgactga agagcggac          39

<210> SEQ ID NO 10
<211> LENGTH: 39
<212> TYPE: DNA
<213> ORGANISM: Artificial Sequence
<220> FEATURE:
<223> OTHER INFORMATION: synthetic PCR amplification primer mCARL R1

<400> SEQUENCE: 10
cgcggcggcc gcatttccat tcaggatgcc ctgctgacc          39

<210> SEQ ID NO 11
<211> LENGTH: 33
<212> TYPE: DNA
<213> ORGANISM: Artificial Sequence
<220> FEATURE:
<223> OTHER INFORMATION: synthetic PCR amplification primer hCAR F1

<400> SEQUENCE: 11
cgcgtcgaca tggcgctcct gctgtgcttc gtg          33

<210> SEQ ID NO 12
<211> LENGTH: 36
<212> TYPE: DNA
<213> ORGANISM: Artificial Sequence
<220> FEATURE:
<223> OTHER INFORMATION: synthetic PCR amplification primer hCAR R2

<400> SEQUENCE: 12
gcgggcggcc gcctatacta tagacccatc cttgct          36

<210> SEQ ID NO 13
<211> LENGTH: 33
<212> TYPE: DNA
<213> ORGANISM: Artificial Sequence
<220> FEATURE:
<223> OTHER INFORMATION: synthetic PCR amplification primer hCARL F1

<400> SEQUENCE: 13
cgcgtcgaca tgttttgccc actgaaactc atc          33

<210> SEQ ID NO 14
<211> LENGTH: 36
<212> TYPE: DNA
<213> ORGANISM: Artificial Sequence
<220> FEATURE:
<223> OTHER INFORMATION: synthetic PCR amplification primer hCARL R2

<400> SEQUENCE: 14
gcgggcggcc gctcaaaagg cttgctgtgt ttttgg          36

<210> SEQ ID NO 15
<211> LENGTH: 36
<212> TYPE: DNA
<213> ORGANISM: Artificial Sequence
<220> FEATURE:
<223> OTHER INFORMATION: synthetic PCR amplification primer hCAR R1

<400> SEQUENCE: 15
gcgggcggcc gctttatttg aaggagggac aacgtt                                36

<210> SEQ ID NO 16
<211> LENGTH: 36
<212> TYPE: DNA
<213> ORGANISM: Artificial Sequence
<220> FEATURE:
<223> OTHER INFORMATION: synthetic PCR amplification primer hCARL R1

<400> SEQUENCE: 16
gcgggcggcc gcattaccac ccaagaccag aggcct                                36

<210> SEQ ID NO 17
<211> LENGTH: 365
<212> TYPE: PRT
<213> ORGANISM: Homo sapiens
<220> FEATURE:
<223> OTHER INFORMATION: human Coxackie virus and Adenovirus receptor
      (CAR)

<400> SEQUENCE: 17

Met Ala Leu Leu Leu Cys Phe Val Leu Leu Cys Gly Val Val Asp Phe
 1               5                  10                  15

Ala Arg Ser Leu Ser Ile Thr Thr Pro Glu Glu Met Ile Glu Lys Ala
                20                  25                  30

Lys Gly Glu Thr Ala Tyr Leu Pro Cys Lys Phe Thr Leu Ser Pro Glu
            35                  40                  45

Asp Gln Gly Pro Leu Asp Ile Glu Trp Leu Ile Ser Pro Ala Asp Asn
        50                  55                  60

Gln Lys Val Asp Gln Val Ile Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Gly Leu Ile Ala
225                 230                 235                 240

```
Gly Ala Ile Ile Gly Thr Leu Leu Ala Leu Ala Leu Ile Gly Leu Ile
            245                 250                 255

Ile Phe Cys Cys Arg Lys Lys Arg Arg Glu Glu Lys Tyr Glu Lys Glu
        260                 265                 270

Val His His Asp Ile Arg Glu Asp Val Pro Pro Lys Ser Arg Thr
    275                 280                 285

Ser Thr Ala Arg Ser Tyr Ile Gly Ser Asn His Ser Ser Leu Gly Ser
290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Thr Pro Gln Ser Pro Thr Leu Pro
                325                 330                 335

Pro Ala Lys Val Ala Ala Pro Asn Leu Ser Arg Met Gly Ala Ile Pro
            340                 345                 350

Val Met Ile Pro Ala Gln Ser Lys Asp Gly Ser Ile Val
        355                 360                 365

<210> SEQ ID NO 18
<211> LENGTH: 352
<212> TYPE: PRT
<213> ORGANISM: Mus musculus
<220> FEATURE:
<223> OTHER INFORMATION: mouse Coxackie virus and Adenovirus receptor
      (CAR)

<400> SEQUENCE: 18

Met Ala Arg Leu Leu Cys Phe Val Leu Leu Cys Gly Ile Ala Asp Phe
1               5                   10                  15

Thr Ser Gly Leu Ser Ile Thr Thr Pro Glu Gln Arg Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ser Asp Asn
    50                  55                  60

Gln Ile Val Asp Gln Val Ile Leu Tyr Ser Gly Asp Lys Ile Tyr
65                  70                  75                  80

Asp Asn Tyr Tyr Pro Asp Leu Lys Gly Arg Val His Phe Thr Ser Asn
                85                  90                  95

Asp Val Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Phe Leu Leu Thr Val Leu Val Lys Pro Ser Gly Thr
    130                 135                 140

Arg Cys Phe Val Asp Gly Ser Glu Glu Ile Gly Asn Asp Phe Lys Leu
145                 150                 155                 160

Lys Cys Glu Pro Lys Glu Gly Ser Leu Pro Leu Gln Phe Glu Trp Gln
                165                 170                 175

Lys Leu Ser Asp Ser Gln Thr Met Pro Thr Pro Trp Leu Ala Glu Met
            180                 185                 190

Thr Ser Pro Val Ile Ser Val Lys Asn Ala Ser Ser Glu Tyr Ser Gly
        195                 200                 205

Thr Tyr Ser Cys Thr Val Gln Asn Arg Val Gly Ser Asp Gln Cys Met
    210                 215                 220

Leu Arg Leu Asp Val Val Pro Pro Ser Asn Arg Ala Gly Thr Ile Ala
225                 230                 235                 240
```

-continued

```
Gly Ala Val Ile Gly Thr Leu Leu Ala Leu Val Leu Ile Gly Ala Ile
                245                 250                 255

Leu Phe Cys Cys His Arg Lys Arg Arg Glu Glu Lys Tyr Glu Lys Glu
            260                 265                 270

Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
    290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Ala Pro Gln Ser Pro Thr Leu Ala
            325                 330                 335

Pro Ala Lys Phe Lys Tyr Ala Tyr Lys Thr Asp Gly Ile Thr Val Val
            340                 345                 350

<210> SEQ ID NO 19
<211> LENGTH: 63
<212> TYPE: DNA
<213> ORGANISM: Artificial Sequence
<220> FEATURE:
<223> OTHER INFORMATION: synthetic multi-cloning site insert

<400> SEQUENCE: 19
cgcggatcct aattaattaa ggtttaaact gtcgacgaat tcgcggccgc cacgcgttcg      60
cga                                                                   63
```

METHODS FOR DETECTING TH1 CELLS

CROSS-REFERENCES TO RELATED APPLICATIONS

The present application is a divisional of U.S. application Ser. No. 13/207,837, filed Aug. 11, 2011, now abandoned, which is a divisional of U.S. application Ser. No. 11/568,435, filed Mar. 28, 2008, which issued as U.S. Pat. No. 8,017,344 on Sep. 13, 2011, which is a U.S. National Phase of PCT/JP2005/008150, filed Apr. 28, 2005, which claims the benefit of Japanese Application No. 2004-133093, filed on Apr. 28, 2004, the disclosures of which are hereby incorporated herein by reference in their entirety.

TECHNICAL FIELD

The present invention relates to methods for detecting Th1 cells, which are helper T cells thought to be involved in cellular immunity. Specifically, the present invention relates to methods for detecting Th1 cells using antibodies against coxsackie virus and adenovirus receptor (CAR) or against CAR ligand (CARL), a ligand on Th1 cells and binds to CAR. When the ratio between Th1 and Th2 cells in biological samples is examined by the methods described above, patients from whom the biological samples were collected can be diagnosed for atopic diseases. The present invention also relates to methods of screening for inhibitors of the binding between CAR and CARL. The present invention further relates to antibodies that inhibit the binding between CAR and CARL, and cell adhesion inhibitors and therapeutic agents for contact dermatitis comprising these antibodies.

BACKGROUND ART

Immune reactions in the body take place locally, and are commonly characterized by the infiltration of immune cells. Specifically, efficient immune reactions are not achieved without adequate mobilization of the required immune cells to local sites. Further, the types of infiltrating immune cell vary depending on the tissues and diseases. For example, a large number of Th1 cells producing interleukin (IL)-12, interferon (IFN)-$\gamma$, or such accumulate in joints with rheumatoid arthritis, while many Th2 cells producing IL-4, IL-5, or such accumulate in asthmatic lungs. By elucidating the cell infiltration mechanism allowing such selective cell infiltration, it is thought that infiltration of specific cells can be suppressed and the diseases of immune reactions can thereby be controlled.

The infiltration of immune cells is roughly divided into four steps: (1) loose contact with vascular endothelial cells via secretin; (2) integrin activation by chemokine receptors; (3) strong adhesion to vascular endothelial cells via integrins; and (4) extravascular migration through intercellular spaces between vascular endothelial cells. The molecular mechanisms underlying the first three steps have been elucidated; however, the extravascular migration is still poorly understood.

JAM-A and PECAM-1 have recently been reported as molecules involved in extravascular migration. JAM-A and PECAM-1 are cell membrane proteins belonging to the immunoglobulin superfamily (IgSF), and function as cell adhesion molecules.

The JAM family, comprising JAM-A, JAM-B, and JAM-C, comprise two extracellular Ig-like domains and are reported as being expressed in epithelial cells, endothelial cells, leukocytes, platelets, and the like. In addition to homophilic binding, binding to integrin $\alpha L\beta 2$ has been reported for JAM-A. Binding to integrin $\alpha 4\beta 1$ and JAM-C, in addition to homophilic binding, have been reported for JAM-B. JAM-C has been reported as binding to JAM-B and integrin $\alpha M\beta 2$, but not as binding in a homophilic manner. Thus, through such homophilic or heterophilic binding, JAM family molecules are involved in adhesion between endothelial cells, between leukocytes and endothelial cells, and between platelets and endothelial cells.

In addition to the JAM family, many other molecules comprising two extracellular Ig-like domains exist. There are reports that some of these show similar localizations to molecules of the JAM family. For example, the coxsackie and adenovirus receptor (CAR) was identified as a receptor for coxsackie viruses and adenoviruses and is localized in tight junctions and adherence junctions in epithelial cells and endothelial cells (Non-Patent Documents 1 and 2). Further, the endothelial-selective adhesion molecule (ESAM) was identified as a molecule selectively expressed only in endothelial cells, but was then reported as being expressed in platelets as well.

To control diseases involving immune cells, it is extremely important to investigate whether such molecules belonging to IgSF are associated with the adhesion of epithelial cells, endothelial cells, leukocytes, and platelets, and to elucidate the mechanism underlying cell infiltration.

[Non-Patent Document 1] Cohen C. J., Shieh J. T., Pickles R. J., Okegawa T., Hsieh J. T., Bergelson J. M., Proc. Natl. Acad. Sci. USA, (2001) 98(26):15191-15196.

[Non-Patent Document 2] Walters R. W., Freimuth P., Moninger T. O., Ganske I., Zabner J., Welsh M. J., Cell, (2002) 110(6):789-799.

[Non-Patent Document 3] Moog-Lutz C., Cave-Riant F., Guibal F. C., Breau M. A., Di Gioia Y., Couraud P. O., Cayre Y. E., Bourdoulous S., Lutz P. G., Blood, (2003) 102(9):3371-3378.

DISCLOSURE OF THE INVENTION

Problems to be Solved by the Invention

Cell adhesion molecules with the ability to adhere to specific lymphocytes are thought to contribute to the selective cellular infiltration of those lymphocytes, and thus by identifying these cell adhesion molecules and their ligands, it is expected that cellular infiltration of specific lymphocytes can be suppressed and the diseases of immune reactions can be controlled. A purpose of the present invention is thus to search for cell adhesion molecules with the ability to mediate cell adhesion to specific lymphocytes, to identify ligands for these molecules, and to discover uses for these adhesion molecules, ligands, and antibodies against them.

To search for cell adhesion molecules with the ability to adhere to activated lymphocytes, the present inventors conducted cell adhesion experiments on activated lymphocytes using chimeric molecules formed between secretory alkaline phosphatases and the extracellular domains of candidate molecules belonging to IgSF. As a result, CAR was revealed to function as an adhesion molecule for activated lymphocytes.

Next, monoclonal antibodies against CAR were produced, and three types of CAR-specific antibodies (4C9, 5E9, and 5G11) were obtained. Cell adhesion mediated by homophilic binding of CAR was inhibited by 5G11 and increased by 4C9 and 5E9. Moreover, cell adhesion between CAR and activated lymphocytes was inhibited by 4C9 and 5G11, but suppression was not observed with 5E9. It was thus suggested that the activity of antibodies in inhibiting cell adhesion depends on the antibody binding site.

CAR expression in activated lymphocytes was investigated using the anti-CAR antibodies. Expression of CAR protein was undetectable on cell surfaces, and expression of CAR mRNAs was also not detectable. This suggested that the homophilic binding of CAR did not mediate the cell adhesion of activated lymphocytes, and that an unknown ligand(s) for CAR is expressed in activated lymphocytes. Thus, first, the possibility that the unknown ligand for CAR was an integrin was examined. The effect on cell adhesion of antibodies against CD11a, CD18, CD29, CD49d, CD51, and CD61 was assessed. However, none of the antibodies inhibited adhesion between CAR and activated lymphocytes.

Moreover, to identify the unknown CAR ligands, the state of lymphocytes that adhere to CAR was investigated. Activated lymphocytes were revealed to adhere to CAR when stimulated with IL-2, but not when stimulated with IL-15. Neither cells of the T cell line TK1, nor resting CD4+ T cells adhered to CAR. Furthermore, binding to the cell surface of various lymphocytes was examined using chimeric proteins (CAR-AP) formed between alkaline phosphatase (AP) and extracellular regions of CAR. CAR-AP bound to IL-2-stimulated activated lymphocytes, but not to IL-15-stimulated activated lymphocytes, nor to cells of the T cell line TK1, nor to resting CD4+ T cells.

Next, the possibility that unknown CAR ligands were IgSF members was investigated. Mouse Ensembl database was searched to investigate the chromosomal positions of CAR and the molecules of the JAM family. These molecules formed discrete clusters on chromosomes 1, 9, and 16. 50 IgSF molecules existing near CAR and the molecules of the JAM family were selected, and their expression in various lymphocytes was investigated using real-time PCR. The results showed that ENSMUSG0000048534 exhibited an expression pattern that correlated to the adhesion activity to CAR. Then, to examine whether or not ENSMUSG0000048534 was an unknown CAR ligand, chimeric proteins formed between the extracellular domain of this molecule and alkaline phosphatase were prepared and examined for the activity of adhering to B300 cells and CAR-expressing B300 cells. As a result, only CAR-expressing B300 cells adhered, and adhesion was inhibited by 5G11. These results revealed that ENSMUSG0000048534 was a novel CAR ligand on lymphocytes, and ENSMUSG0000048534 was thus named CARL (CAR ligand).

A gene encoding CARL was found on mouse chromosome 9 (46.9 Mb). The gene encoding CARL and a mouse cDNA sequence of unknown function deposited in GenBank as "similar to AMICA (BC050133)" matched. A gene for a human homolog of CARL is thought to be the human cDNA sequence AMICA (AY138965) deposited in GenBank, which is located on the mouse chromosome homology region on human chromosome 11 (117.6 Mb) and has a high amino acid sequence homology, but whose function is unknown. A human AMICA molecule lacking a portion of the amino acid sequence (human JAML (AJ515553)) has been recently reported as an adhesion molecule expressed in bone marrow-derived cells (Non-Patent Document 3). Analyses of protein-protein interactions using BIAcore revealed that CAR and CARL extracellular domains directly bound and their association affinity constant was 4.8 nM. In addition, it was shown that CARL was selectively expressed in Th1 cells among lymphocytes, and that CAR selectively adhered to Th1 cells among lymphocytes in a manner dependent on CARL expression.

Further, cells expressing CARL lacking one of the two putative Ig-like domains (domains 1 and 2) were each prepared and tested for their activity in adhering to the CAR-AP chimeric proteins. As a result, B300 cells expressing full-length CARL and B300 cells expressing CARL lacking domain 2 adhered to CAR-AP chimeric proteins, while B300 cells expressing CARL lacking domain 1 did not. Thus, domain 1 of CARL was revealed to be required for binding between CAR and CARL.

Next, #3 monoclonal antibody specific to CARL was obtained. CARL expression in Th1 and Th2 cells was investigated using this #3 antibody, revealing a strong expression selectively in Th1 cells. The #3 antibody inhibited the adhesion of CAR-expressing B300 cells to CARL-AP proteins. Further, the #3 antibody bound to CARL on the membrane of B300 cells expressing full-length CARL and B300 cells expressing CARL lacking domain 2, but did not bind to those of B300 cells expressing CARL lacking domain 1. Thus the #3 antibody, which has the activity of inhibiting binding was revealed to recognize domain 1, which is required for binding between CAR and CARL.

CARL expression in cells other than Th1 cells was investigated, and CARL was found to be strongly expressed in neutrophils. Further, when the produced #3 anti-CARL antibody was used in a mouse model for contact dermatitis to conduct therapeutic experiments, a therapeutic effect was observed.

Human CARL-AP chimeric proteins were tested for their adhesion activity to B300 cells expressing human CAR, and binding between human CAR and human CARL was detected. Likewise, human CAR-AP chimeric proteins and human CARL-AP chimeric proteins were tested for adhesion activity to B300 cells expressing human CARL, and binding between human CAR and human CARL was detected. Thus, the phenomena observed in mice were also confirmed in humans. Further, monoclonal antibodies against human CARL were prepared, and antibodies that inhibited the binding of CARL to CAR-expressing cells were discovered. As was the case in mice, anti-human CARL antibodies were also shown to have an activity of inhibiting cell adhesion and a therapeutic activity against contact dermatitis.

To summarize the above, the present inventors showed that: CAR functions as an adhesion molecule for lymphocytes; CARL is a novel CAR ligand on lymphocytes; CARL is expressed selectively in Th1 cells; Th1 cells selectively adhere to CAR; domain 1 is required for binding between CAR and CARL; and human and mouse CAR and CARL show similar characteristics. Thus, the present invention relates to methods and kits for detecting Th1 cells, which use the direct interaction between CAR and CARL. In another embodiment, the present invention provides methods for detecting Th1 cells by using antibodies against CARL, which was identified as a novel ligand on Th1 cells. By such detection of Th1 cells, the ratio between Th1 and Th2 cells in biological samples can be examined, and subjects from whom the biological samples were collected can be diagnosed for atopic diseases. The present invention thus relates to methods for examining the ratio between Th1 and Th2 cells, and methods for diagnosing atopic diseases based on the examined ratio.

In yet another embodiment, the present invention relates to methods of screening for inhibitors of the binding between CAR and CARL. The present invention also relates to antibodies that inhibit the binding between CAR and CARL, and to compositions that inhibit cell adhesion, which comprise such antibodies, for example, compositions for treating contact dermatitis.

More specifically, the present invention provides the following:

[1] a method for detecting a Th1 cell, which comprises the steps of:
(a) contacting a cell sample comprising a lymphocyte with a CAR; and
(b) detecting a cell that bound to a CAR in step (a);
wherein a CAR is a protein that binds to a polypeptide comprising the amino acid sequence of SEQ ID NO: 1 or 2, and is a protein comprising the amino acid sequence of any one of:
(1) an amino acid sequence of a natural CAR;
(2) an amino acid sequence encoded by a polynucleotide that hybridizes under stringent conditions to a polynucleotide encoding a natural CAR;
(3) an amino acid sequence with a deletion, substitution, addition, or insertion of one or more amino acid residues in the amino acid sequence of a natural CAR;
(4) an amino acid sequence with 90% or more homology to an amino acid sequence of a natural CAR;
(5) an amino acid sequence comprising an extracellular domain of an amino acid sequence of an above (1) to (4); or
(6) a fusion amino acid sequence of a marker protein and a protein of an above (1) to (5);
[2] the method of [1], wherein the CAR is bound to a carrier;
[3] a kit for detecting a Th1 cell, which comprises a CAR as a detection reagent;
[4] the kit of [3], wherein the CAR is bound to a carrier;
[5] a method for detecting a Th1 cell, which comprises the steps of:
(a) contacting a cell sample comprising a lymphocyte with an anti-CARL antibody; and
(b) detecting a cell that bound to the anti-CARL antibody in step (a);
wherein the anti-CARL antibody is an antibody that binds specifically to a CARL, and wherein the CARL is a protein that binds to a natural CAR and is the protein of any one of:
(1) a protein comprising the amino acid sequence of SEQ ID NO: 1;
(2) a protein comprising an extracellular domain of the amino acid sequence of SEQ ID NO: 1;
(3) a protein comprising the amino acid sequence of SEQ ID NO: 2;
(4) a protein comprising an extracellular domain of the amino acid sequence of SEQ ID NO: 2;
(5) a protein comprising an Ig-like domain 1 of an amino acid sequence of an above (1) to (4);
(6) a protein encoded by a polynucleotide that hybridizes under stringent conditions to the cDNA sequence of SEQ ID NO: 3 or 4;
(7) a protein comprising an amino acid sequence encoded by a polynucleotide that hybridizes under stringent conditions to a polynucleotide encoding an amino acid sequence of a protein of the above (1) to (5);
(8) a protein comprising an amino acid sequence with 90% or more homology to an amino acid sequence of a protein of the above (1) to (5); or
(9) a protein comprising an amino acid sequence with a deletion, substitution, addition, or insertion of one or more amino acid residues in an amino acid sequence of a protein of the above (1) to (5);
[6] the method of [5], wherein the anti-CARL antibody is bound to a carrier;
[7] a method for examining the ratio between Th1 cells and Th2 cells, which comprises the method of [1] or [5];
[8] a method for determining whether a subject from whom a cell sample is collected is affected with an atopic disease based on the ratio between Th1 cells and Th2 cells, which is examined by the method of [7];
[9] a kit for detecting a Th1 cell, which comprises an anti-CARL antibody as a detection reagent;
[10] the kit of [9], wherein the anti-CARL antibody is bound to a carrier;
[11] the kit of [9] that determines whether a subject from whom a cell sample is collected is affected with an atopic disease;
[12] a method of screening for an inhibitor of the binding between a CAR and a CARL, which comprises the steps of:
(a) contacting a CAR and a CARL in the presence of a test substance;
(b) detecting the binding between the CAR and the CARL in step (a);
(c) comparing the degree of binding between the CAR and the CARL, detected in step (b), with that in the absence of the test substance; and
(d) selecting as an inhibitor to the binding between CAR and CARL a test substance that suppresses the binding between the CAR and the CARL compared to in the absence of the test substance;
wherein the CARL is a protein that binds to a natural CAR, and is the protein of any one of:
(1) a protein comprising the amino acid sequence of SEQ ID NO: 1;
(2) a protein comprising an extracellular domain of the amino acid sequence of SEQ ID NO: 1;
(3) a protein comprising the amino acid sequence of SEQ ID NO: 2;
(4) a protein comprising an extracellular domain of the amino acid sequence of SEQ ID NO: 2;
(5) a protein comprising an Ig-like domain 1 of the amino acid sequence of an above (1) to (4);
(6) a protein encoded by a polynucleotide that hybridizes under stringent conditions to the cDNA sequence of SEQ ID NO: 3 or 4;
(7) a protein comprising an amino acid sequence encoded by a polynucleotide that hybridizes under stringent conditions to a polynucleotide encoding an amino acid sequence of a protein of the above (1) to (5);
(8) a protein comprising an amino acid sequence with a deletion, substitution, addition, or insertion of one or more amino acid residues in the amino acid sequence of a protein of an above (1) to (5);
(9) a protein comprising an amino acid sequence with 90% or more homology to an amino acid sequence of a protein of an above (1) to (5); or
(10) a fusion protein between a marker protein and a protein of the above (1) to (8); and
wherein the CAR is a protein that binds to a polypeptide comprising the amino acid sequence of SEQ ID NO: 1 or 2, and is a protein comprising an amino acid sequence of any one of:
(11) an amino acid sequence of a natural CAR;
(12) an amino acid sequence encoded by a polynucleotide that hybridizes under stringent conditions to a polynucleotide encoding a natural CAR;
(13) an amino acid sequence with a deletion, substitution, addition, or insertion of one or more amino acid residues in the amino acid sequence of a natural CAR;
(14) an amino acid sequence comprising an extracellular domain of an amino acid sequence of an above (11) to (13); or
(15) a fusion amino acid sequence of a marker protein and the protein of the above (14);

[13] the method of [12], wherein either the CAR or the CARL is bound to a carrier;

[14] the method of [12], wherein the CAR and/or the CARL are expressed in a host cell using an expression vector;

[15] an antibody that inhibits the binding between a CAR and a CARL, wherein a CARL is a protein of any one of:

(1) a protein comprising the amino acid sequence of SEQ ID NO: 1;

(2) a protein comprising an extracellular domain of the amino acid sequence of SEQ ID NO: 1;

(3) a protein comprising the amino acid sequence of SEQ ID NO: 2;

(4) a protein comprising an extracellular domain of the amino acid sequence of SEQ ID NO: 2;

(5) a protein comprising an Ig-like domain 1 of an amino acid sequence of an above (1) to (4);

(6) a protein encoded by a polynucleotide that hybridizes under stringent conditions to the cDNA sequence of SEQ ID NO: 3 or 4;

(7) a protein comprising an amino acid sequence encoded by a polynucleotide that hybridizes under stringent conditions to a polynucleotide encoding an amino acid sequence of a protein of an above (1) to (5);

(8) a protein comprising an amino acid sequence with 90% or more homology to an amino acid sequence of a protein of an above (1) to (5); or (9) a protein comprising an amino acid sequence with a deletion, substitution, addition, or insertion of one or more amino acid residues in the amino acid sequence of a protein of an above (1) to (5);

[16] the antibody of [15], wherein the CAR and the CARL are derived from a human;

[17] the antibody of [15] or [16], wherein the antibody is an anti-CAR antibody;

[18] the antibody of [17], wherein the anti-CAR antibody is produced by hybridoma @mCAR:5E9-1-1 deposited under Accession Number: FERM BP-10317, hybridoma @mCAR:5G11-1-1-11 deposited under Accession Number: FERM BP-10318, or hybridoma @mCAR:4C9-1-1 deposited under Accession Number: FERM BP-10320;

[19] the antibody of [15] or [16], wherein the antibody is an anti-CARL antibody;

[20] the antibody of [19], wherein the anti-CARL antibody is produced by hybridoma @mCARL:#3.11 deposited under Accession Number: FERM BP-10319;

[21] a cell adhesion inhibitor comprising the antibody of any one of [15] to [20]; and

[22] a therapeutic agent for contact dermatitis, which comprises the antibody of any one of [15] to [20].

BRIEF DESCRIPTION OF THE DRAWINGS

FIG. 6 shows cell adhesion between CAR and CAR ligand (CARL), and the inhibition of cell adhesion by anti-CAR antibodies.

FIG. 7 is a diagram showing the amino acid sequence of CARL (SEQ ID NO:1).

BEST MODE FOR CARRYING OUT THE INVENTION

Figure 1:
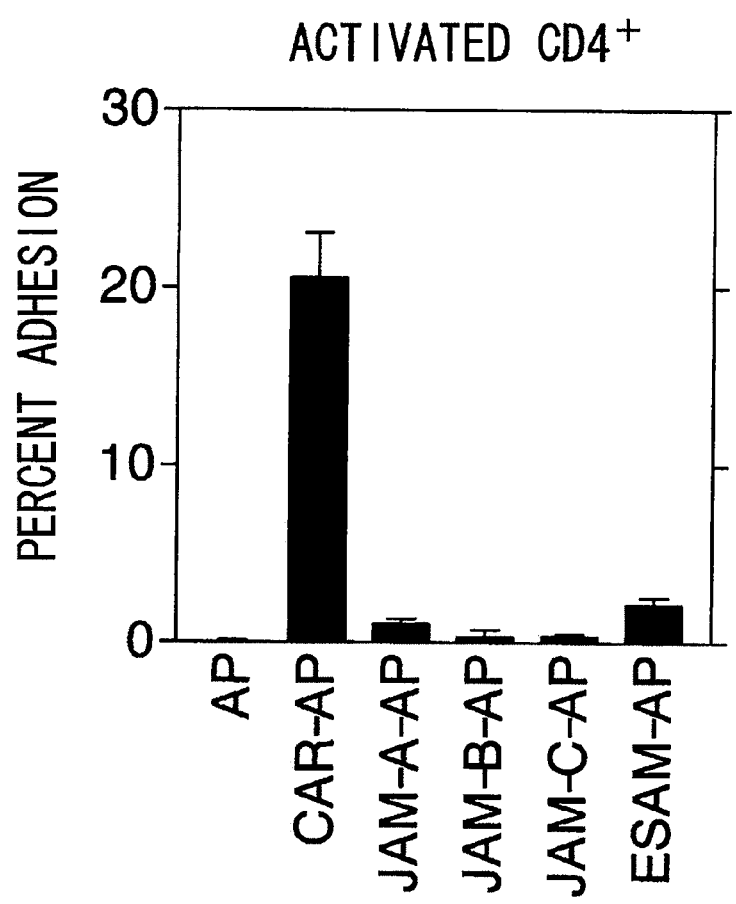
FIG. 1 is a diagram showing that CAR functions as an adhesion molecule for activated T cells.

Methods for Detecting Th1 Cells Using CAR

The present invention demonstrated that CAR binds to Th1 cells via direct binding with CARL, which is specifically expressed on Th1 cells. The present invention thus relates to methods for detecting Th1 cells using CAR. Specifically, the present invention provides methods for detecting Th1 cells, which comprise the steps of:

(a) contacting cell samples comprising lymphocytes with CAR; and (b) detecting the cells that bound to CAR in step (a).

The "cell samples comprising lymphocytes" in the present detection methods are not particularly limited, and examples include blood cell samples expected to comprise lymphocytes, such as bone marrow and peripheral blood. Peripheral blood is particularly preferred for convenience of collection.

Cell samples are typically contacted with CAR by adding polypeptides to reaction solutions comprising cells. For example, the cell adhesion buffer (RPMI1640, 0.5% BSA, and 20 mM HEPES (pH 7.4)) described in Example 4 can be used as a reaction solution comprising cells. However, the present invention is not limited to this, and contact may also be carried out in any reaction solutions, as long the stability of CAR and Th1 cells is maintained and their binding is not inhibited.

Herein, "CAR" and "CAR polypeptide" comprise human proteins comprising amino acid sequences (NP_001329; SEQ ID NO:17) encoded by the nucleotide sequence deposited in GenBank under accession number NM_001338 as well as their allelic variants, splicing variants, and natural CARs, such as proteins derived from mammals other than humans and which correspond to these proteins. Further, in addition to the natural CARs described above, "CAR" and "CAR polypeptide" comprise non-natural polypeptides functionally equivalent to these CARs. "CAR" and "CAR polypeptide" comprise, for example, proteins with an altered amino acid sequence from natural CARs (altered CAR) and CARs produced as recombinant proteins (recombinant CARs). More specifically, "CAR" and "CAR polypeptide" comprise:

(1) amino acid sequences of natural CARs;

(2) amino acid sequences encoded by polynucleotides that hybridize under stringent conditions with polynucleotides encoding natural CARs;

(3) amino acid sequences with a deletion, substitution, addition, or insertion of one or more amino acid residues in the amino acid sequence of a natural CAR;
(4) amino acid sequences with 90% or higher homology to an amino acid sequence of a natural CAR;
(5) amino acid sequences comprising an extracellular domain of an amino acid sequence of the above (1) to (4); and
(6) amino acid sequences obtained by fusing a marker protein with a protein described in the above (1) to (5).

In the present description, "CAR" and "CAR polypeptide" are used interchangeably.

Mammals other than humans from which natural CARs are derived comprise, for example, mice (GenBank NP_034118; SEQ ID NO:18), rats, rabbits, dogs, horses, cats, pigs, bovine, goats, sheep, and primates such as monkeys, gorillas, and chimpanzees. Allelic variants and the proteins derived from these mammals can be obtained, for example, by obtaining cDNAs or genes encoding the allelic variants or proteins from cDNA libraries, genomic libraries, or such using probes or primers produced based on the nucleotide sequences or amino acid sequences of CAR described above and applying known techniques such as hybridization and PCR (Sambrook et al. (1989) Molecular Cloning: A laboratory manual, 2nd ed., Vol. 1-3, Cold Spring Harbor Laboratory Press; Current Protocols in Molecular Biology, John Wiley & Sons (1987-1997); DNA Cloning 1: core techniques, a practical approach 2nd ed., Oxford Univ. (1995)), then expressing these genes. Alternatively, CAR may also be prepared by conventional protein synthesis methods based on known amino acid sequences.

As described above, "CAR" and "CAR polypeptide" comprise the natural CARs described above as well as polypeptides functionally equivalent to these CARs. The functions of CARs can be confirmed, for example, based on binding with CARLs of the animals, such as the protein comprising of the amino acid sequence of SEQ ID NO: 1 in case of mice or SEQ ID NO: 2 in case of humans. Proteins sharing biological activity are known to generally be conserved evolutionarily at the amino acid sequence level, as well as at the level of the genes encoding the proteins. Thus, examples of polypeptides functionally equivalent to natural CARs comprise proteins exhibiting high amino acid sequence homology to a natural CAR, particularly in their active sites. Human AMICA, a counterpart of mouse CARL that binds to CAR, had a homology of 37.4% over the entire amino acid sequence. In the present invention, high amino acid sequence homology means, for example, an identity of 30%, 35%, 40%, or 50% or more, preferably 60% or more, more preferably 70% or more (for example, 80%, 90%, or 95% or more). Herein, the term "% identity" is defined as the percentage of matching between amino acid residues (conservative substitutions not comprised in "matching") when two amino acid sequences are aligned, permitting spaces as required to yield a maximal value between the two sequences. Such amino acid sequence % identity can be calculated using known software (BLAST (see Altschul et al. (1990) J. Mol. Biol. 215:403-410; on the world wide web at ncbi.nlm.nih.gov.), BLAST-2, MegAlign, and such). One skilled in the art can appropriately determine each adjustable parameter required for the calculation of identity using such known software, after considering the sensitivity or the like.

Genes encoding proteins that exhibit high amino acid sequence homology and comparable activity to a natural CAR can be obtained using conventional techniques, such as hybridization and PCR, using probes or primers produced based on known amino acid sequences or gene sequences of a natural CAR (Sambrook et al. (1989) Molecular Cloning: A laboratory manual 2nd ed., Vol. 1-3, Cold Spring Harbor Laboratory Press). Proteins with biological activities equivalent to those of a natural CAR can be obtained by expressing these genes. Thus, the "CAR" and "CAR polypeptide" described in the present description comprise proteins comprising amino acid sequences encoded by polynucleotides that hybridize under stringent conditions to polynucleotides encoding a natural CAR. Examples of hybridization conditions for use in the present invention include "2×SSC, 0.1% SDS, 50° C.", "2×SSC, 0.1% SDS, 42° C.", and "1×SSC, 0.1% SDS, 37° C.". Conditions of higher stringency include "2×SSC, 0.1% SDS, 65° C.", "0.5×SSC, 0.1% SDS, 42° C.", and "0.2×SSC, 0.1% SDS, 65° C.". More specifically, a method that uses the Rapid-hyb buffer (Amersham Life Science) can be carried out by performing pre-hybridization at 68° C. for 30 minutes or more, adding a probe to allow hybrid formation at 68° C. for one hour or more, washing three times in 2×SSC/0.1% SDS at room temperature for 20 minutes per wash, washing three times in 1×SSC/0.1% SDS at 37° C. for 20 minutes per wash, and finally washing twice in 1×SSC/0.1% SDS at 50° C. for 20 minutes per wash. This may also be carried out using, for example, the Expresshyb Hybridization Solution (CLONTECH), by performing pre-hybridization at 55° C. for 30 minutes or more, then adding a labeled probe and incubating at 37° C. to 55° C. for one hour or more, washing three times in 2×SSC/0.1% SDS at room temperature for 20 minutes per wash, and washing once at 37° C. for 20 minutes with 1×SSC/0.1% SDS. Herein, conditions of higher stringency can be achieved by setting a high temperature (for example, 60° C. or 68° C.) for pre-hybridization, hybridization, and the second wash. In addition to salt concentration of the buffer and temperature, one skilled in the art can also integrate other hybridization factors, such as probe concentration, probe length, nucleotide sequence composition of the probe, and reaction time, to obtain CAR isoforms and allelic variants, and corresponding genes derived from other species. Molecular Cloning: A Laboratory Manual $2^{nd}$ ed. (Cold Spring Harbor Press (1989)), Current Protocols in Molecular Biology (John Wiley & Sons (1987-1997)), DNA Cloning 1: Core Techniques, A Practical Approach $2^{nd}$ ed. (Oxford University (1995)) and such can be used as laboratory manual for the hybridization method.

In the present description, "CAR" and "CAR polypeptide" further comprise proteins with altered amino acid sequences from a natural CAR described above. Examples of such an "altered CAR" and "altered CAR polypeptide" include proteins in which a region that is not involved in the binding of a natural CAR with CARL has been deleted. Examples of particularly preferred proteins in which a portion of a natural CAR has been deleted include polypeptides comprising an amino acid sequence comprising an extracellular domain of a natural CAR. Protein domains can be predicted at domain searching sites, for example, at on the world wide web at smart.embl-heidelberg.de/. Other than the above, the altered CARs and altered CAR polypeptides of the present invention also comprise proteins in which one or more amino acid residues of a natural CAR or a suitable polypeptide chain is attached to a natural CAR, and proteins comprising an amino acid sequence with a substitution or insertion of one or more amino acid residues in the amino acid sequence of the natural CAR. Methods for deleting, adding, substituting, or inserting into a protein with a known amino acid sequence, arbitrary amino acid residues of the sequence are known. Such proteins can be produced, for example, by performing a site-directed mutagenesis, which is a known technique (see, for example, Nucleic Acid Research, Vol. 10, No. 20, p. 6487-6500, 1982), to DNAs encoding them. In the present description, the phrase "one or more amino acids" means a number of amino acids that can be added, deleted, or substituted by performing site-directed mutagenesis one or more times. Site-directed mutagenesis can be performed, for example, as described below using synthetic oligonucleotide primers containing the desired mutations in the complementary strand to the phage DNAs to be mutagenized. Specifically, the aforementioned synthetic oligonucleotides are used as primers to synthesize strands complementary to the phage DNAs, and host cells are transformed with the obtained double-stranded DNAs. The cultures of transformed bacteria are plated on agar, and single cells containing the phages are allowed to form plaques. In such cases, theoretically 50% of the new colonies contain phages comprising the mutations in the single-stranded phage DNAs, while the remaining 50% comprise the original sequence. The obtained plaques are hybridized with synthetic probes labeled by kinase treatment at a temperature at which those that completely match with the DNAs comprising the above desired mutations would hybridize, but those comprising the original strand would not hybridize. Then, those plaques that hybridize to the probe are selected, and DNAs are recovered after culture.

In addition to the above-described site-directed mutagenesis, methods for substituting, deleting, or inserting one or more amino acids into the amino acid sequences of biologically active peptides, such as enzymes, without loss of their activities, include methods in which genes are treated with mutagens and methods in which genes are selectively cleaved, selected nucleotides are deleted, added, or substituted, and the genes are ligated.

The CARs and CAR polypeptides used in the present invention can also be altered as described below by using known methods. When one or more arbitrary amino acid residues in the amino acid sequence of a natural CAR are replaced with other amino acid residues, substitution with conservative amino acid residues are preferred. Conservative amino acid residues indicate amino acids comprising side chains similar to the amino acid residues prior to substitution. Amino acids can be categorized, for example, into the nine groups shown below, according to the chemical properties of their side chains (hereinafter amino acids are represented by one-letter symbols): (1) neutral hydrophobic side chain (A, F, L, M, P, V, and W); (2) neutral polar side chain (C, G, N, Q, S, T, and Y); (3) basic side chain (H, K, and R); (4) acidic side chain (D and E); (5) aliphatic side chain (A, G, I, L, and V); (6) aliphatic hydroxyl side chain (S and T); (7) amine-containing side chain (H, K, N, Q, and R); (8) aromatic side chain (F, W, and Y); and (9) sulfur-containing side chain (C and M). In addition, proteins in which one or more amino acid residues in a natural CAR are modified by glycosylation, phosphorylation, or the like and proteins modified by deglycosylation or dephosphorylation using chemical and enzymatic techniques, are also comprised in the altered CARs and altered CAR polypeptides of the present invention. Such altered CARs may also be used as CARs and CAR polypeptides in the present invention. Such protein alterations and modifications can be carried out with the aim to improve the stability and biological activity of CARs and CAR polypeptides. By measuring binding activity to CARL, for example, such altered or modified proteins can be confirmed as retaining their activities or otherwise. Herein, the phrase "retain biological activity" does not necessarily mean the same activity level as that of a natural CAR, and the activity may be higher or lower than the original activity.

The CARs and CAR polypeptides used in the present invention can be produced as recombinant proteins as well as isolated from natural sources as described above. "Recombinant CARs" and "recombinant CAR polypeptides" may be produced by expressing them as fusion proteins with marker proteins for convenience of detection; the marker proteins can be, for example, an enzyme such as alkaline phosphatase (SEAP) or β-galactosidase; a binding protein such as maltose-binding protein or glutathione-S-transferase (GST); an Fc region of an antibody; or a fluorescent protein such as green fluorescence protein. Examples of particularly preferred fusion proteins include those in which marker proteins are linked to an extracellular domain of a natural CAR. Recombinant proteins, comprising such fusion proteins, can be produced, for example, using appropriate expression systems, including in vitro systems and host-vector systems.

Generally, expression vectors are first constructed to comprise chimeric genes comprising appropriate transcriptional and translational regulatory regions and sequences encoding proteins of interest operably linked to the regulatory regions. The transcriptional and translational regulatory regions comprise DNA sequences recognized in selected hosts and required for the expression of the protein-coding sequences. Such DNA sequences comprise, for example, promoters, enhancers, polyadenylation signals, operator sequences, ribosome binding sites, initiation signals, and terminators. When eukaryotic cells are used as hosts, expression vectors preferably comprise a promoter/enhancer elements. "Operably" linked or attached means that protein-coding sequences linked downstream of the regulatory regions are transcribed under the regulation of the regulatory regions, without any shift in the reading frame, and expressed in hosts or to extracellular spaces. Appropriate expression vectors to be used for the recombinant CAR polypeptides include known expression vectors for mammalian cells, insect cells, plant cells, yeast cells, and bacterial cells. Alternatively, commercially available vectors may also be used.

Next, host cells are transformed with the constructed expression vectors. Many cell lines have already been established as host cell lines, and various transformation methods suited to such host cell lines have also been established. Any of these known host cell lines may be used to produce recombinant CAR polypeptides, and those skilled in the art can carry out efficient transformation using appropriate introduction methods suited to selected hosts. For example, such transformation methods include, but are not limited to, the following methods: transformation of prokaryotic cells can be carried out by calcium treatment, electroporation, or the like; methods using Agrobacterium and leaf disc methods are known for plant cells; and examples for mammalian cells comprise calcium phosphate precipitation. Other known methods include nuclear microinjection, protoplast fusion, DEAE-dextran method, cell fusion, electroporation, lipofectamine method (GIBCO BRL), and methods using FuGENE6 reagent (Boehringer-Mannheim). For detailed information on mammalian cell transformation, reports of Keown et al. ((1990) Methods in Enzymol. 185:527-537), Mansour et al. ((1988) Nature 336:348-352), and such can be referred to. When natural glycosylation is required, mammalian cells are preferably selected as hosts. Many cell lines, comprising A431, BHK, CHO, COS, CV-1, Hela, HL-60, Jurkat, 205, and 293 cells, are known as such mammalian cells, and these can be used to produce recombinant CAR polypeptides.

In the next step, desired proteins are expressed by culturing transformed cells. Host cells are cultured by known methods suited to the selected cells. For example, when mammalian cells are used as hosts, media such as Dulbecco's modified Eagle medium (DMEM; Virology 8:396 (1959)), minimal essential medium (MEM; Science 122:501 (1952)), RPMI1640 (J. Am. Med. Assoc. 199:519 (1967)), 199 (Proc. Soc. Biol. Med. 73:1 (1950)), Iscove's Modified Dulbecco's Medium (IMDM), or such are used, which can be supplemented as necessary with fetal calf serum (FCS) and such, and culture is carried out at a pH of about 6 to 8, at 30° C. to 40° C. for about 15 to 200 hours. The media may be changed, aerated, and stirred during culture, as required. Recombinant proteins can be secreted to extracellular spaces when secretory signals recognized in the selected host cells are attached to the proteins. The expressed recombinant proteins can be obtained from the host cells, or from the culture media when secreted.

Moreover, transgenic animals (see Susumu (1985) Nature 315:592-594; Lubon (1998) Biotechnol. Annu. Rev. 4: 1-54; and such), transgenic plants, or the like can be prepared as required and made to produce recombinant CAR polypeptides. When producing proteins using transgenic animals, the proteins are preferably expressed in a tissue specific manner (for example, in milk) by using promoters that ensure tissue-specific expression.

The CAR polypeptides used in the present invention may be purified proteins. For example, proteins expressed using recombination techniques can be purified using conventional protein purification means. Known protein purification methods include chromatographies, such as affinity, ion exchange, gel filtration, reverse phase, adsorption, and hydrophobic interaction, as well as methods such as ethanol precipitation, recrystallization, distillation, electrophoresis, dialysis, immunoprecipitation, solvent extraction, and ammonium sulfate precipitation (Strategies for Protein Purification and Characterization: A Laboratory Course Manual, Marshak et al. ed., Cold Spring Harbor Laboratory Press (1996)). Such methods can be used to purify CAR polypeptides. The CAR polypeptides used in the present invention may be purified CAR polypeptides purified by such known means, or in some cases may be partially purified proteins. Moreover, when for example CAR polypeptides are expressed as GST fusion proteins, purification methods using glutathione columns are effective. Meanwhile, nickel column-based purification methods can be used when CAR polypeptides are expressed with attached histidine tags. When CAR polypeptides are produced as such fusion proteins, unnecessary portions may be cleaved using enzymes such as thrombin or factor Xa after purification if required.

CAR polypeptides used in the detection of Th1 cells in the present invention may be used bound onto carriers. The carriers for immobilizing must have no adverse effect on the CAR polypeptides and cells. Such carriers include, for example, synthetic or natural organic polymer compounds; glasses; organic polymer materials, such as polystyrenes; inorganic materials, such as silica gels, alumina, and activated carbons; and such materials surface-coated with polysaccharides, synthetic polymers, and the like. The carrier shapes are not particularly limited, and carriers of any shape can be used as long as they do not impede contact between the polypeptides and cells. Examples comprise membranous, fibrous, granular, hollow fiber-shaped, unwoven, porous, and honeycomb-shaped ones. The polypeptides can be bound, for example, to the inner walls of reaction vessels, such as plates, dishes, and test tubes, and to beads and so on. The areas of contact between polypeptides and cell samples can be controlled by altering the thickness, surface area, diameter, length, shape, and size of the carriers used.

Detection of Th1 cells in the present invention is preferably carried out using known methods after separating lymphocytes, preferably T cells, and more preferably helper T cells from "cell samples comprising lymphocytes"; or by detecting cells co-expressing lymphocyte markers, preferably co-expressing T cell markers, and more preferably co-expressing helper T cell markers, for example CD4, in "cell samples comprising lymphocytes".

When CAR polypeptides are expressed as fusion proteins with marker proteins, methods corresponding to the adopted marker proteins are used as the methods of the present invention for detecting Th1 cells. For example, when enzymes such as alkaline phosphatase or β-galactosidase are used, detection is achieved based on the enzyme activity; when binding proteins such as glutathione-S-transferase or maltose-binding protein are used, detection is achieved based on the binding activity of glutathione or maltose, respectively; when an Fc region of an antibody is used, detection is achieved based on binding with an Fc-binding protein; and when a fluorescent protein such as green fluorescence protein is used, detection is achieved based on fluorescence.

Moreover, when not expressed as fusion proteins with marker proteins, CAR polypeptides bound to Th1 cells can be detected using antibodies against CAR. When using anti-CAR antibodies in the detection, the antibodies used must recognize a part of the CAR polypeptide other than the part that binds to CARL on Th1 cells. Anti-CAR antibodies can be produced by standard methods, in the same way as for the anti-CARL antibodies described in the next section, "Methods for detecting Th1 cells using anti-CARL antibodies". Specific examples of antibody production comprise the method of Example 5. Alternatively, CAR polypeptides may be designed as fusion proteins with other polypeptides recognizable by antibodies, such that they can be detected by using appropriate antibodies (see Examples 3 and 4). Commercially available epitope-antibody systems can also be used (Experimental Medicine 13:85-90 (1995)). CAR polypeptides may be produced as fusion proteins with β-galactosidase, maltose-binding protein, glutathione-S-transferase (GST), green fluorescence protein (GFP), or the like, such that detection can be carried out without using a secondary antibody. In addition, small epitope-antibody systems, such as those of polyhistidine, influenza hemagglutinin HA, human c-myc, FLAG, and T7, are also known. When such tags are attached to CAR polypeptides, the CAR polypeptides can be detected using commercially available antibodies against the tags. Alternatively, when labeled with radioisotopes, CAR polypeptides can be detected using scintillation counters. Moreover, the interactions between CAR polypeptides and Th1 cells can be observed in real time using biosensors that use surface plasmon resonance phenomenon (for example, BIAcore X (BIAcore)), without having to label the polypeptides.

Further, for example, magnetic particles can be used as the carriers, and CAR polypeptides and CARL-expressing cells bound to the polypeptides can be detected and collected using magnets. Magnetic devices for such collection have also been developed and can be used (for example, MACS (Daiichi Pure Chemicals Co.)). Moreover, Th1 cells expressing CARL can also be selected by flow cytometry using cell sorters (FACS) and CAR polypeptides which have been labeled with fluorescence (for example, fluorescein isothiocyanate (FITC) and phycoerythrin) or the like.

Methods for Detecting Th1 Cells Using Anti-CARL Antibodies

The present inventors identified CARL as a CAR ligand on Th1 cells. The present invention thus relates to methods for detecting Th1 cells using anti-CARL antibodies. Specifically, Th1 cells can be detected by the steps of:

(a) contacting anti-CARL antibodies with cell samples comprising lymphocytes; and (b) detecting cells that bound to the anti-CARL antibodies in step (a).

The "cell samples comprising lymphocytes" in the present methods are not particularly limited as in the case of the above-described section "Methods for detecting Th1 cells using CAR", and blood cell samples expected to contain lymphocytes, such as bone marrow and peripheral blood, can be used.

Moreover, cell samples can be contacted with antibodies in appropriate reaction solutions as in the case of the above-described CAR polypeptides.

Herein, "CARL" and "CARL polypeptide" include mouse proteins belonging to IgSF that comprise 379 residues comprising the amino acid sequence of FIG. 7 (SEQ ID NO: 1; GenBank Accession No. AAH50133); their allelic variants and splicing variants; and natural CARLs, such as proteins derived from mammals other than mice and corresponding to these proteins. Further, in addition to the above-described natural CARLs, the "CARL" and "CARL polypeptide" comprise non-natural polypeptides functionally equivalent to these CARLs. For example, "CARL" and "CARL polypeptide" comprise proteins with altered amino acid sequences from natural CARLs (altered CARLs) and CARLs produced as recombinant proteins (recombinant CARLs). In the present description, the terms "CARL" and "CARL polypeptide" are used interchangeably.

A cDNA sequence encoding the protein comprising the amino acid sequence of SEQ ID NO: 1 is deposited under Accession No. BC050133 in GenBank (SEQ ID NO: 3). Moreover, a mouse protein in which 37 amino acids are inserted in place of the first 11 amino acids of BC050133, and the arginine at position 231 is replaced with glutamine, is also known as a variant (GenBank Accession No. XM_194453). Examples of human proteins corresponding to these mice proteins comprise human AMICA protein (GenBank Accession No. AAN52117; SEQ ID NO: 2) encoded by a cDNA sequence of GenBank Accession No. AY138965 (SEQ ID NO: 4). CARL comprises a signal sequence (the underlined portion in FIG. 7) predicted using the SignalIP program, and a transmembrane domain (portion underlined with a dotted line in FIG. 7) predicted using the SMART program. Furthermore, the asparagine residue boxed in FIG. 7 was predicted to be glycosylated by using the ScanProsite program. Also, the cysteine residues labeled with an asterisk (*) in FIG. 7 were predicted to form disulfide bonds. The present invention showed that CARL was expressed selectively in Th1 cells among lymphocytes, and that depending on the expression of CARL, CAR bound selectively to Th1 cells among lymphocytes. Proteins sharing a biological activity are known to be generally conserved evolutionarily at their amino acid sequence level, as well as at the level of genes encoding the proteins. Therefore, examples of mammals, other than mice and humans, from which a "natural CARL" and a "natural CARL polypeptide" of the present invention are derived comprise rats, rabbits, dogs, horses, cats, pigs, bovine, goats, sheep, and primates, such as monkeys, gorillas, and chimpanzees. Allelic variants and the proteins derived from these mammals can be obtained, for example, by obtaining cDNAs or genes encoding the allelic variants or proteins from cDNA libraries, genomic libraries, or such using probes or primers produced based on known nucleotide sequences or amino acid sequences of CARL described above and applying known techniques such as hybridization and PCR, then expressing these genes. Alternatively, CARL may also be prepared by conventional protein synthesis methods (for example, chemical synthesis methods and cell culture methods) based on known amino acid sequences.

In the present invention, "CARL" and "CARL polypeptide" refer to the following proteins that bind to these animals' CAR polypeptides, which are peptides encoded by the nucleotide sequence deposited in GenBank under number BC050133 in the case of mice and peptides encoded by the nucleotide sequence deposited in GenBank under number AY138965 in case of humans:

(1) proteins comprising the amino acid sequence of SEQ ID NO: 1 (mouse CARL);
(2) proteins comprising an extracellular domain of the amino acid sequence of the above (1);
(3) proteins comprising the amino acid sequence of SEQ ID NO: 2 (human CARL);
(4) proteins comprising an extracellular domain of the amino acid sequence of the above (2);
(5) proteins comprising the Ig-like domain 1 of the amino acid sequences of the above (1) to (4);
(6) proteins encoded by polynucleotides that hybridize under stringent conditions to a cDNA sequence of SEQ ID NO: 3 (mouse cDNA) or SEQ ID NO: 4 (human cDNA);
(7) proteins comprising the amino acid sequences encoded by polynucleotides that hybridize under stringent conditions to polynucleotides encoding the amino acid sequence of a protein of the above (1) to (5);
(8) proteins comprising amino acid sequences with 90% or higher sequence homology to the amino acid sequence of a protein of the above (1) to (5); and
(9) proteins comprising amino acid sequences with a deletion, substitution, addition, or insertion of one or more amino acid residues in the amino acid sequence of a protein of the above (1) to (5).

Genes encoding CARLs exhibiting biological activities equivalent to those of a CARL of SEQ ID NO: 1 or 2 can be obtained by hybridization by referring to the explanation on the hybridization conditions for obtaining CAR polypeptides described in the above section "Methods for detecting Th1 cells using CAR". Amino acid sequences with a deletion, substitution, addition, or insertion of one or more amino acid residues and exhibiting biological activities equivalent to those of a CARL of SEQ ID NO: 1 or 2 can be obtained by referring to the explanation of the methods for deleting, adding, substituting, or inserting amino acid residues for obtaining CAR polypeptides described in the above section "Methods for detecting Th1 cells using CAR".

The anti-CARL antibodies of the present invention used for detecting Th1 cells may be any antibodies as long as they can bind to CARL on Th1 cells, and comprise polyclonal antibodies, monoclonal antibodies, chimeric antibodies, single-chain antibodies (scFV; Huston et al. (1988) Proc. Natl. Acad. Sci. USA 85: 5879-5883; The Pharmacology of Monoclonal Antibody, Vol. 113, Rosenburg and Moore ed., Springer Verlag (1994) p. 269-315), humanized antibodies, multispecific antibodies (LeDoussal et al. (1992) Int. J. Cancer Suppl. 7:58-62; Paulus (1985) Behring Inst. Mitt. 78:118-132; Millstein and Cuello (1983) Nature 305:537-539; Zimmermann (1986) Rev. Physiol. Biochem. Pharmacol. 105: 176-260; Van Dijk et al. (1989) Int. J. Cancer 43: 944-949), and antibody fragments comprising antigen-binding sites, such as Fab, Fab', F(ab')2, and Fv. Further, the anti-CARL antibodies may be modified by PEG or the like, as required. Alternatively, the antibodies may be produced as fusion proteins with β-galactosidase, maltose-binding protein, GST, green fluorescence protein (GFP), or the like, such that detection can be carried out without using a secondary antibody. Also, by labeling the antibodies with biotin or the like, the antibodies can be collected using avidin, streptavidin, or such.

The anti-CARL antibodies can be produced using CARL, fragments thereof, or cells expressing any one of these, as sensitizing antigens. When a CARL fragment is used as an antigen, a CARL extracellular region is preferably used. If required (for example, when using a short antigen fragment), the fragment may be conjugated with carriers, such as bovine serum albumin, keyhole limpet hemocyanin, and ovalbumin, and then used as an immunogen. Furthermore, if required, known adjuvants, such as aluminium adjuvant, Freund's complete or incomplete adjuvants, or pertussis adjuvant, can be used to enhance the immune response against such antigens.

For example, mammals can be immunized with CARL or fragments thereof, together with an adjuvant as required, to obtain polyclonal antibodies against CARL as sera from the animals. Animals of Rodentia, Lagomorpha, and Primates are typically used as immunized mammals herein, although they are not limited thereto. Examples comprise Rodentia such as mice, rats, and hamsters; Lagomorpha such as rabbits; Primates, comprising monkeys such as crab-eating macaques, Rhesus monkeys, baboons, and chimpanzees. Immunization of the animals is carried out by: appropriately diluting and suspending a sensitizing antigen in PBS or physiological saline; further adding an adjuvant and emulsifying if required; and then injecting intraperitoneally, subcutaneously, or into the footpad. Then, a sensitizing antigen combined with Freund's incomplete adjuvant is preferably administered several times every four to 21 days. Antibody production can be verified by measuring antibody levels in the sera of the immunized animals. The obtained sera comprising the antibodies may be further purified, if required.

Meanwhile, monoclonal antibodies can be produced by the following procedure: first, the spleen are excised from animals immunized by the method described above. Immune cells are separated from the spleen and fused with appropriate myeloma cells using polyethylene glycol or such to produce hybridomas. Regarding cell fusion, reports such as that of Galfre and Milstein ((1981) Methods Enzymol. 73:3-46) can be referred to. Herein, examples of particularly suited myeloma cells comprise cells that allow drug selection of fused cells. When such myeloma enabling drug selection are used, cells are cultured in a culture medium in which cells other than fused cells are killed (such as HAT medium) and fused cells are selectively collected. Then, clones producing antibodies that bind to CAR are selected from the produced hybridomas. The selected clones are transplanted in the peritoneal cavities of mice or such, and ascites fluid can be collected from the animals to obtain monoclonal antibodies.

Hybridomas can also be obtained by first using an immunogen to sensitize human lymphocytes that have been infected by EB virus in vitro, then fusing the sensitized lymphocytes with human-derived myeloma cells (such as U266) to obtain hybridomas that produce human antibodies (Japanese Patent Application Kokai Publication No. (JP-A) S63-17688 (unexamined, published Japanese patent application)). In addition, human antibodies can also be obtained by using antibody-producing cells generated by sensitizing transgenic animals which have the repertoire of human antibody genes (WO 92/03918; WO 93/02227; WO 94/02602; WO 94/25585; WO 96/33735; WO 96/34096; Mendez et al. (1997) Nat. Genet. 15: 146-156, etc.). Methods that do not use hybridomas are exemplified by methods in which antibodies are produced by introducing cancer genes to immortalize immune cells, such as antibody-producing lymphocytes.

The present invention also comprises human monoclonal antibodies. The monoclonal antibodies can be produced by immunizing human antibody-producing nonhuman transgenic mammals, such as human antibody-producing transgenic mice, with immunogens (antigens), such as CARL or fragments thereof, or cells expressing any of these, and then producing monoclonal antibodies according to existing conventional methods for producing monoclonal antibodies.

Specifically, for example, nonhuman transgenic mammals producing human antibodies are immunized with an antigen, in combination with Freund's adjuvant if required. Polyclonal antibodies can be prepared from sera obtained from the immunized animals. Moreover, monoclonal antibodies can be produced by preparing fused cells (hybridomas) from antibody-producing cells obtained from the immunized animals and myeloma cells that lack the ability to secrete endogenous immunoglobulin, cloning the hybridomas, then selecting clones producing monoclonal antibodies that exhibit specific affinity for the antigen used to immunize the mammals.

More specifically, the antibodies can be produced as described below. Specifically, the nonhuman transgenic mammals producing human antibodies (particularly preferred are the "human antibody-producing transgenic mice" described below) are immunized with a desired antigen, in combination with Freund's adjuvant if required, by injecting or transplanting the antigen once or several times subcutaneously, intramuscularly, intravenously, intraperitoneally, or into footpads.

Typically, immunization is carried out one to four times approximately every one to 14 days from the first immunization, and antibody-producing cells are obtained from the immunized mammals approximately one to five days after the final immunization. The frequency and time intervals of immunization can be appropriately varied depending on the properties of the antigens being used, or the like.

Fused cells (hybridomas) that secrete human monoclonal antibodies can be prepared by the method of Köhler and Milstein (Nature, Vol. 256, p. 495-497, 1975) or modified methods based on this method. Specifically, they are prepared by fusing antibody-producing cells from the spleen, lymph nodes, bone marrow, tonsilla, or such, preferably from the spleen, of human antibody-producing nonhuman transgenic mammals immunized as described above, and myeloma cells lacking the ability to secrete endogenous immunoglobulin, which are derived from mammals such as preferably mice, rats, guinea pigs, hamsters, rabbits, or humans, more preferably mice, rats, or humans.

Myeloma cells that can be used in cell fusion include, for example, the mouse-derived myelomas P3/X63-AG8.653 (ATCC No. CRL-1580), P3/NSI/1-Ag4-1 (NS-1), P3/X63-Ag8.U1 (P3U1), SP2/O-Ag14 (Sp2/O, Sp2), NS0, PAI, F0, and BW5147; the rat-derived myelomas 210RCY3-Ag.2.3.; the human-derived myelomas U-266AR1, GM1500-6TG-A1-2, UC729-6, CEM-AGR, D1R11, and CEM-T15. Screening for cells producing monoclonal antibodies (for example, hybridomas) can be performed, for example, by culturing cells in microtiter plates, then measuring the reactivity of culture supernatants from wells in which proliferation was observed to the aforementioned immunogen used for the immunization, by using, for example, enzyme immunoassays such as RIA (radioimmunoassay) and ELISA (enzyme-linked immunosorbent assay).

Monoclonal antibodies can be produced from hybridomas in vitro, or in vivo in the ascites fluid and such of mice, rats, guinea pigs, hamsters, rabbits, and the like, preferably of mice or rats, and more preferably of mice, and isolated from the obtained culture supernatants or from the ascites fluid of the mammals.

Moreover, the monoclonal antibodies of the present invention can be produced on a large scale by using the method described below.

(1) Genes (cDNAs or the like) encoding the heavy and light chains of the monoclonal antibodies are cloned from the hybridomas.
(2) Expression vectors are prepared by inserting the cloned genes encoding the heavy and light chains each into a different or a same vector.
(3) The vectors are introduced into fertilized eggs of desired nonhuman mammals (such as goats).
(4) The fertilized eggs into which the genes have been introduced are transplanted in the uteri of foster mothers to obtain nonhuman chimeric animals.
(5) The chimeric goats are further crossed with other nonhuman mammals to create transgenic nonhuman mammals (bovine, goats, sheep, pigs, or such) in which the genes encoding the heavy and light chains are integrated in the endogenous genes.
(6) The monoclonal antibodies derived from the human monoclonal antibody genes are obtained on a large scale from milk of the nonhuman transgenic mammals (Nikkei Science, April 1997, p. 78-84).

Human monoclonal antibodies produced by this method are also included in the present invention. When cells producing the monoclonal antibodies are cultured in vitro, it is possible to use any known nutrition media or nutrition media prepared based on known basal media that is used to grow, maintain, and preserve hybridomas and to produce monoclonal antibodies in culture supernatants, according to various criteria, such as the characteristics of the cell types to be cultured, the purpose of the experimental studies, and the culture methods.

Basal media include, for example, low calcium media such as Ham's F12 medium, MCDB 153 medium, and low calcium MEM; and high calcium media such as MCDB 104 medium, MEM, D-MEM, RPMI1640 medium, ASF104 medium, and RD medium. The basal media can contain, for example, sera, hormones, cytokines, and/or various inorganic or organic substances depending on the purposes.

Monoclonal antibodies can be purified or isolated by subjecting the culture supernatants or ascites fluid described above to saturated ammonium sulfate, euglobulin precipitation methods, caproic acid methods, caprylic acid methods, ion exchange chromatography (DEAE, DE52, and the like), or affinity column chromatography such as anti-immunoglobulin columns or protein A columns.

The human monoclonal antibodies of the present invention also include human monoclonal antibodies comprising heavy and/or light chains that comprise amino acid sequences with a deletion, substitution, or addition of one or more amino acids in the amino acid sequences of the heavy and/or light chains constituting the antibodies.

The anti-CARL antibodies further comprise antibody fragments, as described above. Antibody fragments can be produced by treating the polyclonal or monoclonal antibodies with enzymes such as papain or pepsin. Alternatively, they can be produced by genetic engineering techniques using a gene that encodes an antibody fragment (see Co et al., (1994) J. Immunol. 152: 2968-2976; Better and Horwitz (1989) Methods Enzymol. 178: 476-496; Pluckthun and Skerra (1989) Methods Enzymol. 178: 497-515; Lamoyi (1986) Methods Enzymol. 121: 652-663; Rousseaux et al. (1986) 121: 663-669; Bird and Walker (1991) Trends Biotechnol. 9: 132-137).

Multispecific antibodies comprised in the anti-CARL antibodies include bispecific antibodies (BsAb), diabodies (Db), and such. Multispecific antibodies can be produced by methods such as: (1) chemically coupling antibodies having different specificities with different types of bifunctional linkers (Paulus (1985) Behring Inst. Mitt. 78: 118-132); (2) fusing hybridomas that secrete different monoclonal antibodies and making these hybridoma produce BsAb (Millstein and Cuello (1983) Nature 305: 537-539); or (3) transfecting eukaryotic cell expression systems, such as mouse myeloma cells, with a light chain gene and a heavy chain gene of different monoclonal antibodies (four types of DNA in total), followed by the isolation of a bispecific monovalent portion (Zimmermann (1986) Rev. Physio. Biochem. Pharmacol. 105: 176-260; Van Dijk et al. (1989) Int. J. Cancer 43: 944-949). On the other hand, diabodies are dimer antibody fragments comprising two bivalent polypeptide chains that can be constructed by gene fusion. These can be produced using known methods (see Holliger et al. (1993) Proc. Natl. Acad. Sci. USA 90: 6444-6448; EP404097; WO 93/11161).

The antibodies and antibody fragments can be recovered and purified, not only using protein A or G, but also by using methods similar to those commonly used to purify other proteins (Antibodies: A Laboratory Manual, Harlow and David Lane ed., Cold Spring Harbor Laboratory Press (1988)). For example, when protein A is used to purify the antibodies of the present invention, known protein A columns, such as Hyper D, POROS, and Sepharose F. F. (Pharmacia) can be used. The concentrations of the obtained antibodies can be determined by measuring the absorbance of samples or the antigen binding activities of antibodies in samples.

The antigen binding activities of antibodies can be measured by absorbance measurement, fluorescence antibody methods, enzyme immunoassays (EIA), radioimmunoassays (RIA), enzyme-linked immunosorbent assays (ELISA), or such. When measurements by ELISA are carried out, samples comprising an antibody of interest are added after the protein (a CAR or CARL or portion thereof) is immobilized. Herein, the samples comprising antibodies include culture supernatants of antibody-producing cells and purified antibodies. Next, a secondary antibody that recognizes anti-CARL antibodies is added and the plates are incubated. The plates are then washed, and the label attached to the secondary antibody is detected. Specifically, when the secondary antibody is labeled, for example, with alkaline phosphatase, the antigen binding activity can be measured by adding an enzyme substrate, such as p-nitrophenyl phosphate, and measuring the absorbance. Moreover, antibody activity may be evaluated using commercially available systems, such as BIAcore (Amersham Pharmacia).

The detection of Th1 cells using anti-CARL antibodies of the present invention is preferably carried out after using known methods to separate lymphocytes, preferably T cells, and more preferably helper T cells from "cell samples comprising lymphocytes"; or by detecting in "cell samples comprising lymphocytes" those cells co-expressing lymphocyte markers, preferably cells co-expressing T cell markers, and more cells preferably co-expressing helper T cell markers, for example CD4.

In the methods of the present invention for detecting Th1 cells using anti-CARL antibodies, the antibodies may be immobilized on appropriate carriers before contacting with cells. Alternatively, cell samples can also be contacted with antibodies under conditions that allow the binding of CARL-expressing cells to anti-CARL antibodies, and then cells that bound to the antibodies can be selectively detected or recovered through purification using the affinity of the antibodies. For example, when the anti-CARL antibodies are bound to biotin, cell-antibody complexes can be purified through a contact with plates, columns, and such to which avidin or streptavidin are bound. Moreover, the anti-CARL antibodies may be immobilized on any of the carriers exemplified above for immobilization of CAR.

More specifically, methods for detecting Th1 cells using the anti-CARL antibodies include fluorescence antibody methods (see Monoclonal Antibodies: Principle and Practice, 3rd ed., Academic Press (1996)), ELISA, RIA, immunohistochemical staining, comprising immunohistological staining and immunocytological staining (for example, ABC and CSA methods; see Monoclonal Antibodies: Principle and Practice, 3rd ed., Academic Press (1996)), Western blotting, and immunoprecipitation. When using ELISA, substances that can easily detect antibodies are used as substrates, or enzymes (for example, peroxidases) that produce detectable products are used as labels and substrates are reacted thereto, and the concentration of the substrates or products is measured using spectrophotometers or the like. ELISA also includes sandwich ELISA. In this method, two types of antibodies that bind to different antigenic sites are used, and analysis is carried out by labeling one antibody with an enzyme or such. In RIA, the antibodies are radiolabeled. The labeled antibodies can be detected using scintillation counters or the like. In immunohistochemical staining, antibodies are labeled and reacted to tissues or cells, and then labels are detected using microscopes. Fluorescent substances and enzymes catalyzing reactions that produce a dye are used as labels. In immunoprecipitation, antibodies and cell samples are reacted, and then carriers that bind specifically to immunoglobulins (protein G-Sepharose or the like) are added to the reaction solution to precipitate the cell-antibody complexes.

Moreover, Th1 cells can be detected by detecting the anti-CARL antibodies in the same way as when using CAR polypeptides. Th1 cells expressing CARL can also be selected by, for example, flow cytometry using cell sorters and anti-CARL antibodies labeled with fluorescence or such, or by using biosensors that use the surface plasmon resonance phenomenon. Flow cytometry and methods using magnets as carriers are particularly simple techniques, and are preferably used in the detection of Th1 cells of the present invention.

Kits for Detecting Th1 Cells

The CAR polypeptides and anti-CARL antibodies described above can be comprised in kits for detecting Th1 cells. The present invention thus relates to kits for detecting Th1 cells, which comprise the CAR polypeptides or anti-CARL antibodies. The CAR polypeptides and anti-CARL antibodies may be comprised in the kits, immobilized on carriers.

In addition to the CAR polypeptides or anti-CARL antibodies, other materials required to detect Th1 cells can be combined in the kits of the present invention. The kits of the present invention can comprise, for example, reagents, containers, devices, and such required to detect the polypeptides and antibodies. The CAR polypeptides or anti-CARL antibodies comprised in the kits, and the other necessary materials may be packed together or separately, or a portion may be packed together. The shape of the packaging is not limited.

The materials required for the detection include, for example, buffers or the like to dilute the polypeptides, antibodies, or cell samples. In addition, the kits may comprise, for example, anti-CAR antibodies for detecting the polypeptides. The kits may also comprise secondary antibodies for detecting antibodies, and when the antibodies are labeled with an enzyme, they may also comprise substrates or the like for the reactions catalyzed by the enzyme. When the polypeptides or antibodies are bound to magnetic particles, magnets and such may be included in the kits. An instruction manual is preferably attached to the kits, describing in detail the detection procedures using the CAR polypeptides or anti-CARL antibodies comprised in the kits of the present invention for detecting Th1 cells. Such instruction manuals can be comprised as pamphlets in the kits, or the instructions may be printed on the packages or such of the kits.

Methods for Examining the Ratio Between Th1 and Th2 Cells

The aforementioned methods for detecting Th1 cells using CAR or anti-CARL antibodies and kits for detecting Th1 cells can be used to examine the ratio between Th1 and Th2 cells in biological samples. Thus, the present invention also relates to methods for examining the ratio between Th1 and Th2 cells. Specifically, helper T cells can be specifically detected in cell samples comprising lymphocytes (for example, using CD4 as a marker) and furthermore, Th1 cells can be detected by the above-described methods for detecting Th1 cells, which use CAR or anti-CARL antibodies. Ratios between Th1 and Th2 cells in cell samples examined as above can be used for diagnosing diseases involving a selective imbalance of Th1 or Th2 cells. For example, it is thought that the Th1 response is dominant in organ-specific autoimmune diseases, while the Th2 response is dominant in cancers, allergies, parasite infections, and the like, and these diseases can be diagnosed using the methods of the present invention for examining the ratio between Th1 and Th2 cells.

Examples of diseases particularly preferably diagnosed by the methods of the present invention for examining the ratio between Th1 and Th2 cells comprise atopic diseases. The present invention thus relates to methods for diagnosing subjects for atopic diseases, based on the ratio between Th1 and Th2 cells determined by methods of the present invention for examining the ratio between Th1 and Th2 cells. Atopic diseases diagnosed by the present methods comprise bronchial asthma, allergic rhinitis, and atopic dermatitis.

Th2 cells are known to be more dominant in such atopic diseases than Th1 cells (Okazaki H. et al. (2002) Clin Exp Allergy. 32(8):1236-1242; and Kim J. H. et al. (2004) J Asthma. 41(8):869-876). Thus, atopic dermatitis can be diagnosed by examining the ratio between Th1 and Th2 cells.

Method of Screening for CAR-CARL Binding Inhibitors

The present invention further provides methods of screening for inhibitors of the binding between CAR and CARL (CAR-CARL binding inhibitors). Specifically, CAR-CARL binding inhibitors are screened by the steps of: (a) contacting CAR and CARL in the presence of test substances; (b) detecting the binding between CAR and CARL in step (a); (c) comparing the degree of the detected binding between CAR and CARL with that in the absence of the test substances; and (d) selecting test substances that suppress the binding between CAR and CARL, as compared to in the absence of the test substance, as inhibitors of the binding between CAR and CARL.

Inhibitors of the binding between CAR and CARL are not limited to particular types of substances. Thus, the test substances to be used in the screening methods of the present invention may be any substances. Examples comprise expression products of gene libraries, libraries of synthetic low-molecular-weight compounds, synthetic peptide libraries, antibodies, substances released from bacteria, cell (microorganisms, plant cells, and animal cells) extracts and culture supernatants, purified or partially purified polypeptides, marine organisms, extracts derived from plants or animals, soil, and random phage peptide display libraries. Inhibitors screened by the present methods inhibit the binding between CAR and CARL, and consequently inhibit adhesion between activated Th1 cells expressing CARL, and epithelial and endothelial cells expressing CAR. Such inhibitors are thus expected to suppress the adhesion of Th1 cells and thereby to alleviate the conditions in diseases such as rheumatoid arthritis, in which the action of Th1 cells is a factor. Therefore, inhibitors obtained by the present screening can be candidates for therapeutic or preventive agents for diseases in which Th1 cells are a factor.

The CAR and CAR polypeptides used herein are those described in the above section "Methods for detecting Th1 cells using CAR". Natural CARs, as well as their fragments, altered forms, modified forms and the like, which retain CARL-binding activity, can be used. The CAR and CAR polypeptides may be produced by expressing them as fusion proteins with marker proteins for convenience of detection, for example enzymes such as alkaline phosphatase (SEAP) and β-galactosidase; binding proteins such as glutathione-S-transferase (GST) and maltose-binding protein; Fc regions of antibodies; or fluorescent proteins such as green fluorescence protein.

Meanwhile, similarly to CAR and CAR polypeptides, the "CARL" and "CARL polypeptides" used in the present invention comprise natural CARLs as well as proteins comprising amino acid sequences altered from natural CARLs, as described in the above section "Methods for detecting Th1 cells using anti-CARL antibodies". CARL polypeptides used in the present methods may be any CARL polypeptides, as long as they retain binding activity to CAR, so they can be used in screening for inhibitors of CAR-CARL binding and are preferably proteins comprising a CARL extracellular domain. Furthermore, examples of polypeptides functionally equivalent to CARL include polypeptides comprising the CAR-binding domain of natural CARL, domain 1 in particular, and proteins exhibiting high amino acid sequence homology to natural CARL, particularly in their active sites. Herein domain 1 is a domain predicted from homology to Ig-like domains, and is, for example, the region comprising the amino acid sequence from position 30 to 139 in SEQ ID NO: 1 and the region comprising the amino acid sequence from position 27 to 136 in SEQ ID NO: 2. Protein domains can be predicted at domain searching sites, for example, on the world wide web at smart.embl-heidelberg.de/. Human AMICA, which corresponds to mouse CARL that binds to CAR, had a homology of 37.4% over its entire amino acid sequence. In the present invention, thus, high homology in the amino acid sequence, means an identity of, for example, 30%, 35%, 40%, or 50% or more, preferably 60% or more, more preferably 70% or more (for example, 80%, 90%, or 95% or more).

In the first step (a), CAR and CARL, which bind each other, are contacted in the presence of a test substance. This contact is typically carried out by adding CARL to a reaction solution comprising CAR and a test substance, or by adding CAR to a reaction solution comprising CARL and a test substance. Reaction solutions used herein are not particularly limited, and any reaction solution may be used, as long as it does not inhibit the reaction between CAR and CARL. Furthermore, the duration of such contact is not particularly limited, and the contact can be long enough for the binding between CAR and CARL, for example, for one, two, three or five minutes or more. Conditions for the contact can be appropriately determined with reference to Example 11, which investigates the affinity between CAR and the CARL extracellular region.

Herein, screening may be carried out with either CAR or CARL bound onto a carrier. The various carriers exemplified in the above section "Methods for detecting Th1 cells using CAR" can be used as the carriers. When one of the polypeptides is immobilized on a carrier, inhibitors are screened, for example, as follows: first, CAR and CARL are contacted in the presence of a test compound. In this example, CAR is assumed to be immobilized. After contact, the carriers are washed thoroughly to wash away CARL that did not bind with CAR. Then, CARL that bound to CAR is detected. CARL can be detected using antibodies against CARL. Alternatively, when labeled CARL is used, the labels can be detected appropriately.

Furthermore, cells expressing either CAR or CARL may be used as a CAR or CARL of the present invention. Such cells may be appropriate host cells into which genes encoding CAR or CARL have been introduced and are expressed on the cell membrane.

Further, CAR-CARL binding inhibitors can be screened using the two-hybrid method (Dalton and Treisman (1992) Cell 68:597-612; Fields and Sternglanz (1994) Trends Genet. 10:286-292). The screening can be performed, for example, using commercially available systems, such as the MATCHMAKER Two-Hybrid system, Mammalian MATCHMAKER Two-Hybrid Assay Kit, and MATCHMAKER One-Hybrid system from Clontech; and the HybriZAP Two-Hybrid Vector System from Stratagene. The two-hybrid method detects the interaction between two types of proteins in vivo using the transcriptional activator GAL4 of a Saccharomyces yeast. GAL4 comprises a DNA binding domain and a transcriptional activation domain, and activates transcription through binding to $UAS_G$, an upstream GAL activation sequence in yeast. Given this, expression vectors encoding fusion proteins are constructed, in which either one of CAR or CARL is fused to the DNA binding domain and the other one is fused to the transcriptional activation domain. Further, an expression vector for a reporter gene operably linked with a promoter comprising the activation sequence $UAS_G$ is prepared, and introduced into host cells along with the above expression vectors for the two fusion proteins. The reporter gene is expressed when the CAR and CARL moieties in the two types of fusion protein bind, and whether CAR and CARL bound can be determined based on this expression. At this time, by including a test substance in the system, inhibition by the test substance of binding between CAR and CARL can be assessed. If a test substance can be encoded by a gene, it may be introduced into host cells as an expression vector constructed to express the gene encoding the substance. Various reporter genes are known and, for example, the Ade2 gene, lacZ gene, CAT gene, luciferase gene, HIS3 gene, β-galactosidase, and β-lactamase can be used.

The interaction between CAR and CARL can be observed in real time using a biosensor which uses the surface plasmon resonance phenomenon (for example, BIAcore (Amersham Pharmacia)), without having to label the polypeptides. Thus, whether a test substance acts as an inhibitor of the binding between CAR and CARL can be detected using such biosensor, by adding the test substance at the time CAR and CARL are contacted. For specific methods Example 11 can be referred to, for example.

CAR-CARL Binding-Inhibiting Antibodies

Furthermore, the present invention relates to antibodies that inhibit the binding between CAR and CARL. The antibodies of the present invention comprise polyclonal antibodies, monoclonal antibodies, chimeric antibodies, single-chain antibodies (scFV; Huston et al. (1988) Proc. Natl. Acad. Sci. USA 85: 5879-5883; The Pharmacology of Monoclonal Antibody, Vol. 113, Rosenburg and Moore ed., Springer Verlag (1994) p. 269-315), humanized antibodies, multispecific antibodies (LeDoussal et al. (1992) Int. J. Cancer Suppl. 7:58-62; Paulus (1985) Behring Inst. Mitt. 78:118-132; Millstein and Cuello (1983) Nature 305:537-539; Zimmermann (1986) Rev. Physiol. Biochem. Pharmacol. 105: 176-260; Van Dijk et al. (1989) Int. J. Cancer 43: 944-949), and antibody fragments comprising antigen-binding sites, such as Fab, Fab', F(ab')2, and Fv. Further, the antibodies of the present invention may be modified by PEG or the like, as required. Alternatively, the antibodies of the present invention may be produced as fusion proteins with β-galactosidase, maltose-binding protein, GST, green fluorescence protein (GFP), or the like, such that detection can be carried out without using a secondary antibody. Also, by labeling the antibodies with biotin or the like, the antibodies can be collected using avidin, streptavidin, or such.

The antibodies of the present invention can be produced using a CAR or fragments thereof, a CARL or fragments thereof, or cells expressing any one of these as sensitizing antigens, by the same method as that used for the anti-CARL antibodies, which is described in the above section "Methods for detecting Th1 cells using anti-CARL antibodies". In a preferred embodiment, the antibodies of the present invention are anti-CAR antibodies or anti-CARL antibodies. The antibodies of the present invention may be, for example, anti-CAR antibodies produced by the hybridomas: @mCAR:5E9-1-1 internationally deposited under Accession Number: FERM BP-10317; @mCAR:5G11-1-1-11 internationally deposited under Accession Number: FERM BP-10318; and @mCAR:4C9-1-1 internationally deposited under Accession Number: FERM BP-10320. Furthermore, the antibodies of the present invention may also be the anti-CARL antibodies produced by hybridoma @mCARL:#3.11 internationally deposited under Accession Number: FERM BP-10319. However, the antibodies of the present invention are not limited to the antibodies described above. As disclosed in detail in the Examples below, for example, the monoclonal antibodies produced by clone 5G11 obtained by the method described in Example 5 inhibit the binding between CAR and Th1 cells. Further, #3 antibody obtained by the method described in Example 14 inhibits the adhesion between CARL and cells expressing CAR, and Example 17 demonstrates that #3 antibody has an effect in the treatment of contact dermatitis. Example 16 shows that monoclonal antibodies #5, #49, and #77 against human CARL inhibit the adhesion between human CARL and cells expressing human CAR.

Hybridomas 5E9, 5G11 and 4C9, obtained in Example 5, and hybridoma #3, obtained in Example 14, were deposited as described below. In the present description, 5E9 is identical to @mCAR:5E9-1-1 described below; 5G11 is identical to @mCAR:5G11-1-1-11 described below; #3 is identical to @mCARL:#3.11 described below; and 4C9 is identical to @mCAR:4C9-1-1 described below. Antibodies produced by these hybridomas are called by the same names as the corresponding hybridomas.

@mCAR:5E9-1-1
(1) Name and address of depositary institution
Name: National Institute of Advanced Industrial Science and Technology, International Patent Organism Depositary
Address: (Postal code: 305-8566) Central 6, 1-1-1 Higashi, Tsukuba-shi, Ibaraki-ken, Japan
(2) Date of international deposit: Apr. 12, 2005 (Date of domestic deposit: Apr. 27, 2004)
(3) International Accession Number: FERM BP-10317
(Domestic Accession Number: P-20031; Domestic Acceptance Number: FERM AP-20031)
 @mCAR:5G11-1-1-11
(1) Name and address of depositary institution
Name: National Institute of Advanced Industrial Science and Technology, International Patent Organism Depositary
Address: (Postal code: 305-8566) Central 6, 1-1-1 Higashi, Tsukuba-shi, Ibaraki-ken, Japan
(2) Date of international deposit: Apr. 12, 2005 (Date of domestic deposit: Apr. 27, 2004)
(3) International Accession Number: PERM BP-10318
(Domestic Accession Number: P-20032; Domestic Acceptance Number: FERM AP-20032)
 @mCARL:#3.11
(1) Name and address of depositary institution
Name: National Institute of Advanced Industrial Science and Technology, International Patent Organism Depositary
Address: (Postal code: 305-8566) Central 6, 1-1-1 Higashi, Tsukuba-shi, Ibaraki-ken, Japan
(2) Date of international deposit: Apr. 12, 2005
(3) International Accession Number: FERM BP-10319
 @mCAR:4C9-1-1
(1) Name and address of depositary institution
Name: National Institute of Advanced Industrial Science and Technology, International Patent Organism Depositary
Address: (Postal code: 305-8566) Central 6, 1-1-1 Higashi, Tsukuba-shi, Ibaraki-ken, Japan
(2) Date of international deposit: Apr. 12, 2005
(3) International Accession Number: FERM BP-10320

Since the antibodies of the present invention inhibit the binding between CAR and CARL, they are expected to suppress the adhesion of Th1 cells and cell adhesion during inflammation, and thus to alleviate diseases. Further, because the binding between CAR and CARL may be involved in the infiltration of Th1 cells, they are expected to be useful in elucidating the mechanism of cell infiltration.

In particular, of the antibodies of the present invention, antibodies prepared using CAR or fragments thereof as antigens can be used to purify CAR or fragments thereof, in the same way as for generic antibodies. They can also be used in drug delivery systems targeting CAR.

Antibodies produced using CARL or fragments thereof as antigens can be used to purify CARL or its fragments, and can be used in drug delivery systems targeting CARL, in the same way as for CAR. Meanwhile, as for the CAR-CARL binding inhibitors described above, the antibodies are expected to suppress the adhesion of Th1 cells in diseases in which the action of Th1 cells is a factor, such as rheumatoid arthritis, and thus to alleviate diseases. These antibodies of the present invention can be candidates for therapeutic or preventive agents for diseases in which Th1 cells are a factor. In fact, the present invention demonstrates that anti-CARL antibodies have an effect in the treatment of contact dermatitis (Example 17).

Compositions Comprising Anti-CAR Antibodies and Compositions Comprising Anti-CARL Antibodies As described above, the antibodies of the present invention inhibit binding between CAR and CARL, and thus can be used to inhibit the adhesion of activated Th1 cells expressing CARL to cells expressing CAR, such as epithelial cells and endothelial cells. Given this, the present invention relates to cell adhesion inhibitors comprising the antibodies of the present invention. Such compositions can be used when examining the binding abilities of CAR and CARL. The inhibitors of the present invention are, for example, the antibodies of the present invention dissolved in appropriate buffers or the like. Further, as required, preservatives, antiseptics, stabilizers, and such can be added within ranges that do not influence the antibody activities.

Furthermore, since the antibodies of the present invention suppress the adhesion of Th1 cells, they are expected to suppress cell infiltration during inflammation, and to be able to alleviate diseases. Thus, compositions comprising such antibodies are expected to be usable as therapeutic or preventive agents for diseases in which the action of Th1 cells is a factor. For example, compositions comprising the antibodies of the present invention can be used as therapeutic or preventive agents for contact dermatitis. In case the antibodies are used as such therapeutic or preventive agents, considering the immunogenicity, it is desirable to use human antibodies or humanized antibodies when the therapeutic or preventive agents are used for humans.

The antibodies can be formulated in consideration of their properties based on known methods for producing antibody preparations. When such compositions of the present invention are used as therapeutic or preventive agents, the compositions comprise the antibodies of the present invention as active ingredients, and physiologically acceptable carriers, excipients, diluents, and such are appropriately mixed in. The mode of administration can be either oral or parenteral administration, but parenteral administration is preferred. Specific examples comprise injections, suppositories, nasal administration, intrapulmonary administration, and percutaneous administration. Injections may be administered locally or systemically by, for example, intravenous administration, intramuscular administration, intraperitoneal administration, subcutaneous administration, intravenous drip infusion, or such. When aiming for administration by injection, the dosage form of the compositions of the present invention can take forms of appropriate combinations with sterile water or physiological saline, emulsifiers, suspending agents, detergents, stabilizers, vehicles, preservatives, and such to formulate effective amounts of the antibodies of the present invention. When aiming for administration as oral preparations, capsules, granules, suspensions, powders, tablets, emulsions, solutions, and such can be selected as the dosage form of the compositions of the present invention.

Examples of emulsifiers or detergents described above comprise stearyl triethanolamine, sodium lauryl sulfate, lauryl amino propionate, lecithin, glyceryl monostearate, sucrose fatty acid ester, and glycerin fatty acid ester.

Examples of suspensions described above comprise, in addition to the detergents described above, for example, hydrophilic polymers such as polyvinyl alcohol, polyvinylpyrrolidone, methylcellulose, hydroxymethylcellulose, hydroxyethylcellulose, and hydroxypropylcellulose.

Examples of stabilizers described above comprise those generally used in medicine.

Examples of vehicles described above comprise those generally used in medicine such as liposomes, microspheres, and lipid vesicles.

Examples of preservatives described above comprise methylparaben, propylparaben, chlorobutanol, benzyl alcohol, phenethyl alcohol, dehydroacetic acid, and sorbic acid.

Sterile compositions for injection can be formulated according to usual formulation operations using oils for injection or aqueous solutions for injection, such as distilled water for injection. Examples of aqueous solutions for injection comprise physiological saline, isotonic solutions comprising glucose or other adjuvants, for example, D-sorbitol, D-mannose, D-mannitol, and sodium chloride. These may be used in combination with appropriate solubilizers, for example, alcohols, specifically ethanol; polyalcohols, for example propylene glycols and polyethylene glycols; nonionic detergents, for example polysorbate 80™ and HCO-50.

Examples of oils for injection comprise sesame oils and soybean oils, which may be used in combination with solubilizers, such as benzyl alcohol or benzyl benzoate. They may also be combined with buffers, for example, phosphate buffers and sodium acetate buffers; soothing agents, for example, procaine hydrochloride; stabilizers, for example, benzyl alcohol and phenol; and antioxidants.

Prepared injections are usually loaded into appropriate ampules. Alternatively, the injections may be prepared in forms where adequate amounts of appropriate vehicles, such as aqueous solutions and oils for injection, are added to ampules containing the freeze-dried antibodies of the present invention at the time of use.

The dose of inhibitors of the present invention just needs to be an amount sufficient to suppress the adhesion of Th1 cells in pathological lesions developed by the effect of Th1 cells, and the doses vary depending on the patient's age, sex, weight, symptoms, and such, as well as the therapeutic purpose, the administration method, and the like. One skilled in the art can determine appropriate doses in consideration of these factors and the activity of selected antibodies. For example, the doses can be selected from a range of one to five times per day, and from a range of 0.0001 to 1000 mg/kg weight, preferably 0.01 to 100 mg/kg weight, and more preferably 0.1 to 10 mg/kg weight per administration. Alternatively, the dose can be selected, for example, from a range of 0.001 to 100000 mg/body, preferably 0.1 to 10000 mg/body, more preferably 1 to 100 mg/body per patient.

All publications cited herein are incorporated by reference into this description.

EXAMPLES

Hereinbelow, the present invention will be specifically described with reference to Examples, but it is not to be construed as being limited thereto.

Example 1

Production of Cells Expressing the Full-Length Adhesion Molecules

The full length cDNAs of the adhesion molecules JAM-A, JAM-B, JAM-C, ESAM, and CAR were cloned as described below. A mouse heart cDNA library (Clontech Quick Clone 7133-1) was used as template for JAM-A, JAM-B, and JAM-C; mouse small intestine cDNAs were used as template for ESAM; and mouse spleen cDNAs were used as template for CAR. The primers for each were designed based on GenBank™ sequences (JAM-A (U89915), JAM-B (AF255911), JAM-C (AJ300304), ESAM (AF361882), and CAR (NM009988)) for amplification by PCR. For example, the primers shown below were used for CAR:

```
                                      (SEQ ID NO: 5)
mCAR F1: GCGGTCGACGCCACCATGGCGCGCCTACTGTGCTTCGTGCT (SEQ ID NO: 6)
mCAR R2: CGCCGCGGCCGCTTATACCACTGTAATGCCATCGGTCT
```

The obtained cDNA fragments were inserted into the expression vector pMXII IRES-EGFP (Oncogene (2000) 19(27):3050-3058) and introduced into the 293/EBNA-1 cell line (Invitrogen) together with the packaging vector pCL-Eco (Imgenex, San Diego, Calif.) to produce recombinant retroviruses. The B300 cell line was infected with this viral solution, and expressing cells were obtained after separating EGFP-positive cells by cell sorting. The 293/EBNA-1 cell line was cultured in Dulbecco's modified Eagle's medium containing 10% FCS, while the B300 cell line was cultured in RPMI-1640 containing 10% FCS and 55 µM 2-mercaptoethanol.

Example 2

Preparation of Activated Lymphocytes

Mouse spleens were ground on a 100 μm mesh and erythrocytes were hemolyzed to obtain splenocytes. CD4-positive cells were isolated from the splenocytes using MACS (Miltenyi Biotec). $4 \times 10^7$ splenocytes were suspended in 70 μl of PBS containing 1% FCS and 2 mM EDTA, and treated with FcR blocking reagent (Miltenyi Biotec). Anti-CD4 antibody-immobilized magnetic beads were added in and the reaction was carried out at 4° C. for 20 minutes. After washing, positive selection was carried out using AutoMACS. The proportion of CD4-positive cells was 90% or more. The purified CD4-positive cells were added to plates with anti-CD3 antibody immobilized at 1 μg/ml, and cultured in the presence of 10 μg/ml anti-CD28 antibody. After two days, 20 ng/ml IL-2 was added and cultured, and activated lymphocytes at seven to nine days after activation were used in experiments.

Example 3

Production of Chimeric Proteins Between Alkaline Phosphatase and the Extracellular Region of Adhesion Molecules First, the pcDNA3.1(+)-SEAP(His)10-Neo vector was produced as follows: the intrinsic SalI site of pCDNA3.1 (+)-Neo vector (CLONTECH) was deleted by SalI digestion followed by blunting. The cDNA fragment SEAP (His)10 was amplified by PCR using pDREF-SEAP His6-Hyg (J. Biol. Chem., 1996, 271, 21514-21521) as template and primers to which HindIII and XhoI have been attached to the 5' end and 3' end, respectively. The resulting cDNA fragments were digested with HindIII and XhoI, then inserted into the pCDNA3.1 (+)-Neo vector from which the SalI site has been deleted.

Next, the extracellular regions of the adhesion molecules were amplified by PCR using the full-length cDNAs obtained in Example 1 as templates and primers to which SalI and NotI have been attached to the 5' end and 3' end, respectively (for example, the primers below were used for CAR).

```
                                        (SEQ ID NO: 5)
mCAR F1: GCGGTCGACGCCACCATGGCGCGCCTACTGTGCTTCGTGCT (SEQ ID NO: 7)
mCAR R1: CGCCGCGGCCGCTCGGTTGGAGGGTGGGACAACGTCTA
```

The amplified cDNA fragments were digested with SalI and NotI, then inserted into the pcDNA3.1(+)-SEAP(His)10-Neo vector described above. The constructs enable the expression of secretory chimeric proteins (hereinafter referred to as AP chimeric proteins) in which the extracellular domains of the adhesion molecules are linked with human secretory placental alkaline phosphatase via a three-amino acid linker (Ala-Ala-Ala), and having a tag of ten histidines (His)10 at the C-terminal. The obtained expression vectors for the AP chimeric proteins were introduced into the 293/EBNA-1 cell line using TransIT LT1 (TAKARA #V2300). The cells were cultured for four to five days. The AP chimeric proteins secreted into the culture supernatant were collected by collecting the culture supernatants by centrifugation and filtering through a 0.22 μm filter. Hepes (pH 7.4) and sodium azide were added thereto until a final concentration of 20 mM and 0.02%, respectively, and the supernatants were stored at 4° C. The concentrations of AP chimeric proteins were calculated after measuring the alkaline phosphatase activity using the Great EscApe Detection kit (CLONTECH #K2041-1).

Example 4

Adhesion of Activated Lymphocytes to Immobilized CAR

Cell adhesion experiments were carried out using AP chimeric proteins to identify molecules functioning as adhesion molecules that adhere to lymphocytes. First, 50 μl of 10 μg/ml anti-alkaline phosphatase antibody (Seradyn MIA1802) was added to 96 well ELISA plates (Nunc), and allowed to stand at 37° C. for 30 minutes to immobilize the antibody. After washing the plates with PBS, the non-specifically binding sites were blocked with BlockAce (Dainippon Pharmaceutical Co.). AP chimeric proteins were diluted to a final concentration of 10 nM, added to the wells, and allowed to stand at room temperature for 30 minutes to immobilize the proteins. Activated lymphocytes were suspended in cell adhesion buffer (RPMI 1640, 0.5% BSA, and 20 mM HEPES (pH 7.4)), fluorescently labeled with Calcein-AM (Dojin), then added to wells at $1 \times 10^5$ cells/well, and incubated at 37° C. for one hour. The non-adherent cells were washed away. A cell lysis solution (10 mM TrisHCl (pH 8.0), 1% TritonX-100) was added, then adherent cells were quantified using Wallac ARVO SX 1420 MULTILABEL COUNTER (Perkin Elmer) and measuring at an excitation wavelength of 485 nm and detection wavelength of 535 nm. The degree of cell adhesion was represented as a percentage ratio of adherent cells to added cells. The extracellular AP chimeric proteins derived from JAM-A, JAM-B, JAM-C, CAR, and ESAM were immobilized, and as a result, CAR was revealed to function as an adhesion molecule that adheres to activated lymphocytes (FIG. 1).

Example 5

Production of Monoclonal Antibodies Against CAR

CAR-AP chimeric proteins were purified for use as antigens for immunization. Purification was carried out using the histidine tags on the C-terminus of the AP chimeric proteins with His Trap Kit (Amersham Biosciences #17-1880-01). Culture supernatant containing a CAR-AP chimeric protein was loaded onto 1 ml HiTrap Chelating HP Column (Amersham #17-0408-01). After washing with a 20 mM imidazole solution, CAR-AP chimeric proteins were eluted from the column using a 500 mM imidazole solution. The concentration of CAR-AP chimeric proteins was calculated from the enzyme activity measurement using the Great EscApe Detection kit (CLONTECH #K2041-1) and protein quantitation using the Protein Assay kit II (BIO-RAD 500-0002JA).

Figure 2:
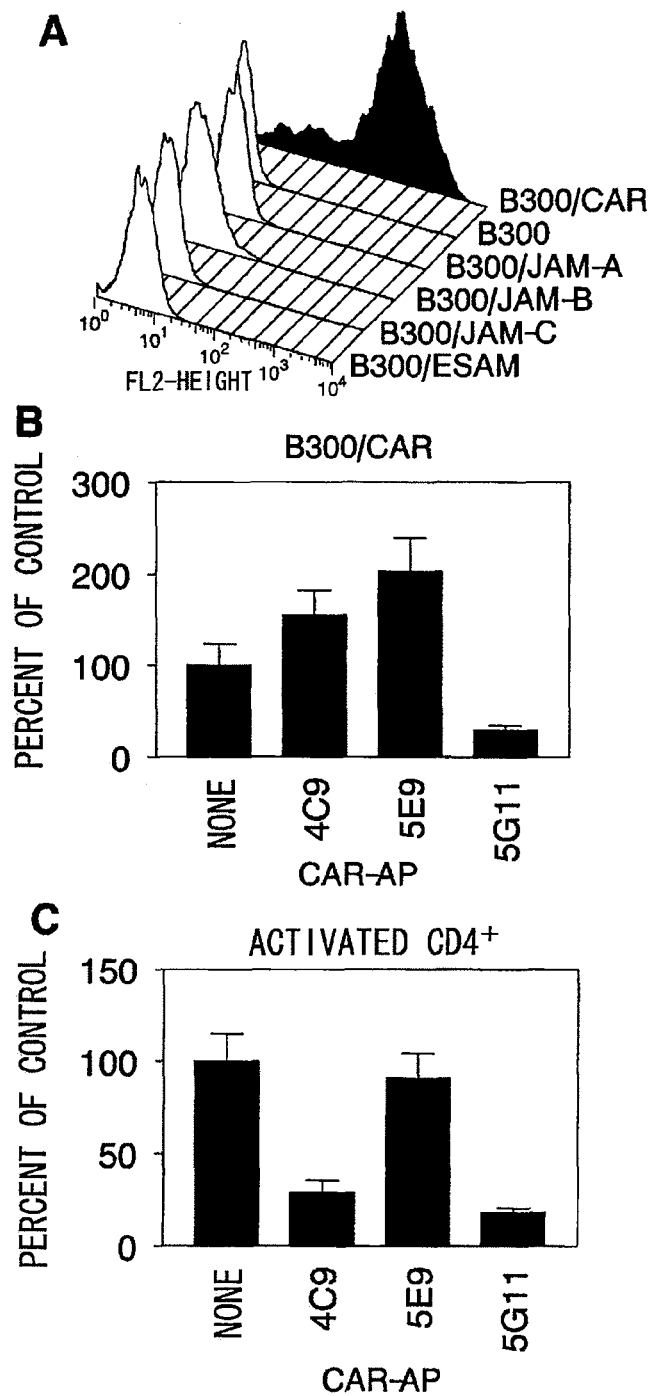
FIG. 2 shows the effect of anti-CAR antibodies on cell adhesion mediated by homophilic binding of CAR.

The obtained CAR-AP chimeric protein was combined with TiterMax, and then used to immunize rats. Lymphocytes were isolated from the immunized rats, mixed such that the ratio of P3 myeloma cells to lymphocytes would be 1:5, and cells were fused using a PEG1500 solution (783-641; Boehringer). Hybridomas were selected using HAT medium (GIBCO BRL 31062-011) and culture supernatants of the obtained hybridomas were screened by sandwich ELISA using CAR-Fc chimeric proteins. Cells from positive wells were cloned, and three types of clone (4C9, 5E9, and 5G11) were obtained. Specificity was examined by FACS and as a result, clone 5G11 reacted only with B300 cells expressing CAR, and did not react with cells of the B300 parental line nor to B300 cells expressing JAM-A, JAM-B, JAM-C, or ESAM (FIG. 2A). The same results were obtained for clones 4C9 and 5E9.

Example 6

Cell Adhesion-Inhibiting Activity of Anti-CAR Antibodies

To investigate the effect of antibodies on cell adhesion mediated by homophilic binding of CAR, 10 µg/ml anti-CAR antibodies were added to B300/CAR cells and the immobilized CAR-AP chimeric proteins, pretreated at room temperature for ten minutes, then the cell adhesion activity in the presence of antibodies was examined. As a result, the adhesion of B300/CAR cells to CAR-AP chimeric proteins was suppressed by antibody 5G11 and increased by antibodies 4C9 and 5E9. The adhesion of activated lymphocytes to CAR-AP chimeric proteins was suppressed by antibodies 4C9 and 5G11, while an increase by antibody 5E9 was not observed (FIGS. 2B and 2C).

Example 7

Existence of Unknown CAR Ligands in Activated Lymphocytes

Figure 3:
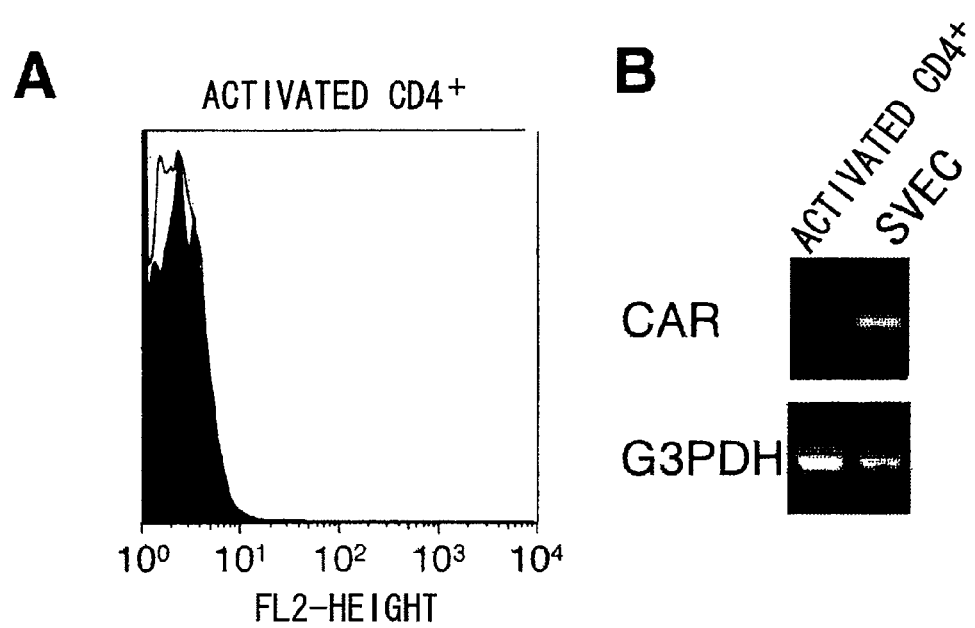
FIG. 3 is a diagram and a photograph showing that CAR is not expressed on activated lymphocytes.

The present inventors examined whether activated lymphocytes expressed CAR and adhered to immobilized CAR-AP chimeric proteins via a homophilic binding. First, the expression of CAR on cell surfaces was examined using anti-CAR antibodies and FACS. Activated lymphocytes were reacted with antibody 5G11, then reacted with PE-labeled goat anti-rat IgG antibodies and assayed using FACSCalibur (Becton Dickinson). However, CAR expression was not detected on the surface of activated lymphocytes (FIG. 3A). Next, the expression of CAR mRNA was examined using RT-PCR; however, mRNA expression was also not detected (FIG. 3B). Therefore, CAR is not expressed in activated lymphocytes, and the existence of an unknown CAR ligand(s) on the surface of lymphocytes was suggested.

Given this, first the possibility that the unknown CAR ligand was an integrin was examined. The present inventors examined the effects of antibodies against CD11a (M17/4 eBioScience 14-0111), CD18 (GAME-46 BD 555280), CD29 (2C9.G2 BD 553343), CD49d (R1-2 BD 553153), CD51 (RMV-7 BD 552299), and CD61 (GAME-46 BD 555280) on cell adhesion. However, none of the antibodies inhibited adhesion between CAR and activated lymphocytes.

Example 8

Figure 4:
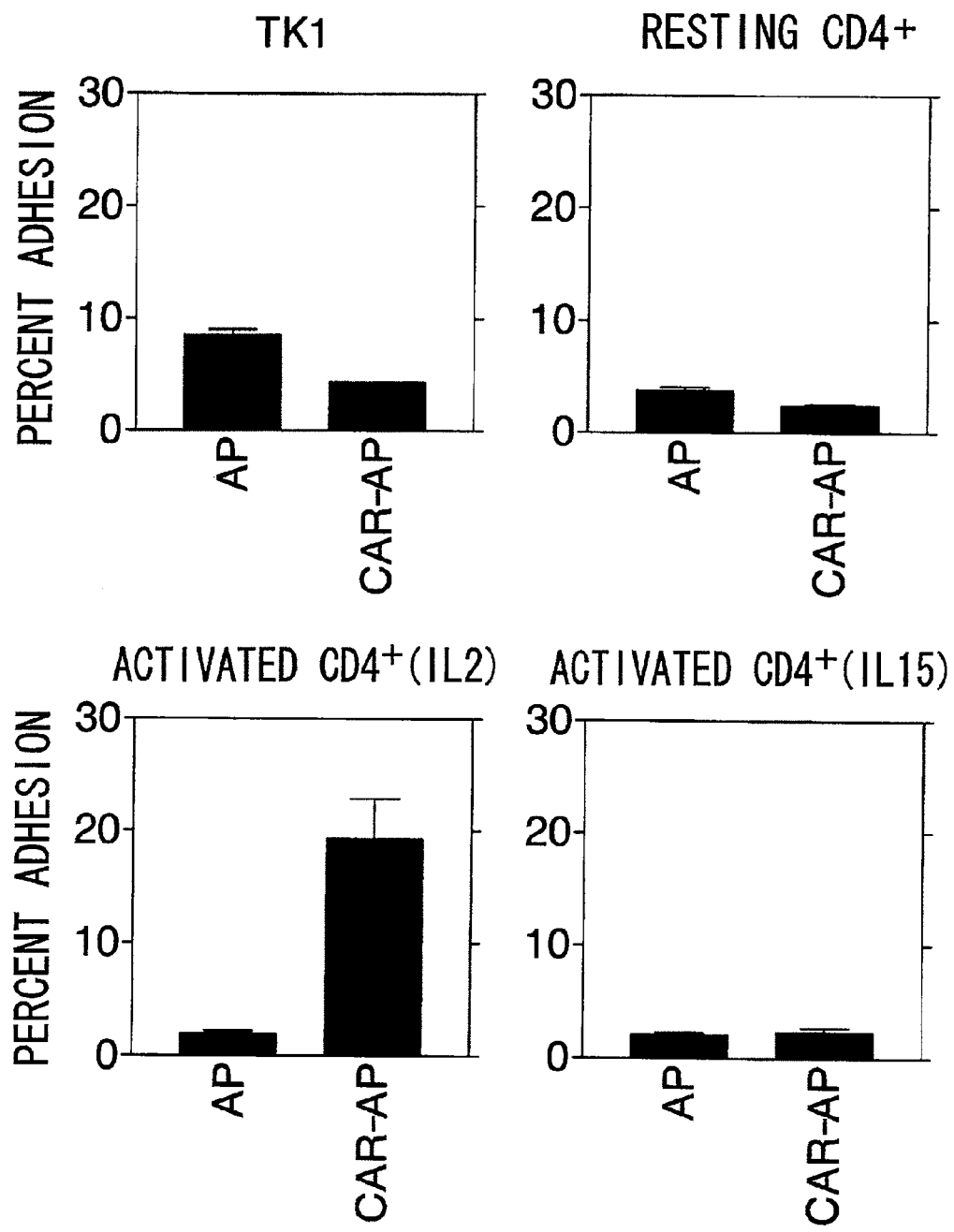
FIG. 4 shows that the activity of cell adhesion to CAR varies depending on the condition of lymphocyte stimulation.

Cell Adhesion Activity of Various Lymphocytes to Immobilized CAR-AP Chimeric Proteins, and Binding Activity of Various Lymphocytes to CAR-AP Chimeric Proteins Next, the characteristics of lymphocytes that adhere to CAR were investigated. The adhesion activity to CAR-AP chimeric proteins of CD4-positive cells (resting CD4+ cells) immediately after purification with MACS, and of activated lymphocytes further cultured for five days in the presence of 20 ng/ml IL-2 or 25 ng/ml IL-15 two days after activation with anti-CD3 antibody, was examined. As a result, the activated lymphocytes which were stimulated with IL-2 adhered, but neither the activated lymphocytes stimulated with IL-15, nor the resting CD4+ cells adhered. The TK1 cell line also did not adhere (FIG. 4).

Figure 5:
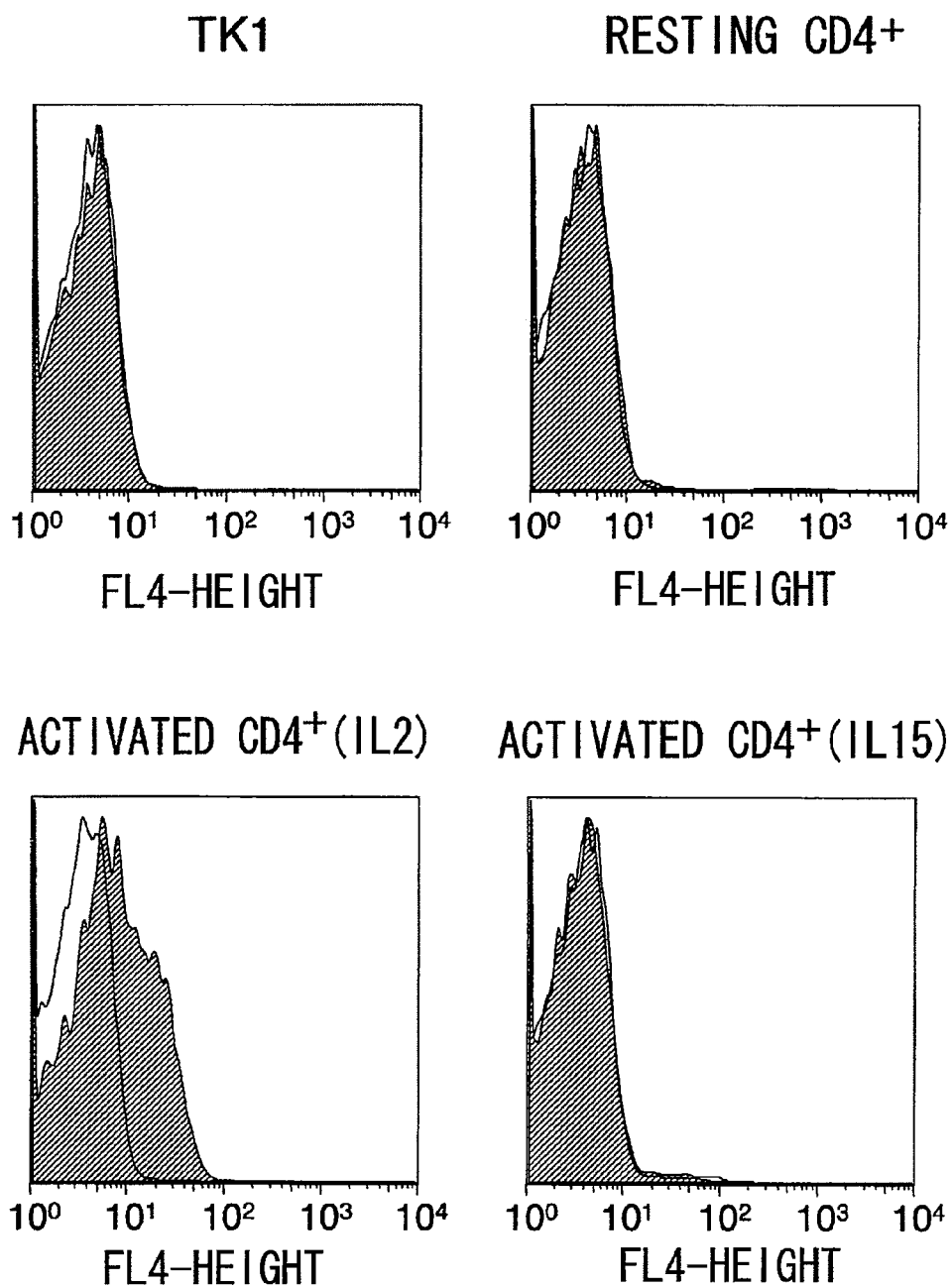
FIG. 5 shows the expression pattern of CAR ligand (CARL).

Next, the binding activity of CAR-AP chimeric proteins to the cell surface of various lymphocytes was investigated. The cells were reacted with 40 nM CAR-AP chimeric proteins at 4° C. for 30 minutes, then reacted with FMAT Blue-labeled mouse anti-alkaline phosphatase antibody at 4° C. for 30 minutes. Binding was detected by FACS. The results revealed that CAR-AP chimeric proteins bound to activated lymphocytes which were stimulated with IL-2, but did not bind to activated lymphocytes which were stimulated with IL-15, nor to resting CD4+ cells nor to the TK1 cell line (FIG. 5).

Example 9

Identification of the Novel Ligand CARL (CAR Ligand) for CAR

Next, the present inventors investigated on the possibility that the unknown ligand for CAR is an IgSF. First, the positional relationships of CAR and JAM family molecules on the mouse chromosomes were investigated. A mouse Ensembl database was searched, and as a result, these molecules existed as discrete clusters formed on chromosomes 1, 9 and 16. Given this, 116 IgSFs existing near CAR and JAM family molecules were focused on and their expression in various lymphocytes was investigated by real-time PCR. Using an RNeasy mini kit (Qiagen, Hilden, Germany), total RNAs were isolated from $5 \times 10^6$ TK1 cells, IL-2-stimulated activated lymphocytes, and IL-15-stimulated activated lymphocytes. The real-time PCR was carried out in the presence of SYBR-green using ABI 7700 Sequence Detection System (PE Applied-Biosystems). As a result, ENS-MUSG0000048534 showed an expression pattern correlating to the activity of adhesion to CAR. Cells expressing this molecule were produced to examine whether ENS-MUSG0000048534 was an unknown CAR ligand. The expressing cells were obtained by the method described in Example 1 using as a template the cDNAs of IL-2-stimulated activated lymphocytes and primers were designed as shown below based on the sequence of ENSMUSG0000048534:

```
mCARL F1:
                                    (SEQ ID NO: 8)
GCGGTCGACGCCACCATGCTTTGCCTCCTGAAACTGATTGTG mCARL R2:
                                    (SEQ ID NO: 9)
CGCGGCGGCCGCTTACTTGGATCTGACTGAAGAGCGGAC
```

Chimeric proteins between AP and the extracellular regions of adhesion molecules (JAM-A, JAM-B, JAM-C, CAR, and ESAM) were prepared similarly as in Example 3. To investigate the homophilic binding of the ligand encoded by ENSMUSG0000048534, a chimeric protein of this ligand with AP was similarly prepared using the following primers:

```
mCARL F1:
                                    (SEQ ID NO: 8)
GCGGTCGACGCCACCATGCTTTGCCTCCTGAAACTGATTGTG mCARL R1:
                                    (SEQ ID NO: 10)
[ID: 1830]CGCGGCGGCCGCATTTCCATTCAGGATGCCCTGCTGACC
```

When the adhesion activities to the extracellular AP chimeric proteins of various adhesion molecules were examined using these expressing cells, the cells only adhered to CAR (FIG. 6A). Furthermore, when the activities of CAR-expressing B300 cells in adhering to the AP chimeric proteins of these extracellular regions were examined, the CAR-expressing B300 cells adhered, and the adhesion was inhibited by 4C9 and 5G11 (FIG. 6B). The results described above revealed that ENSMUSG0000048534 was a novel CAR ligand on lymphocytes and the ligand was named CARL (CAR ligand).

Example 10

Properties of CARL

CARL is a molecule comprising 379 amino acids and belonging to IgSF, and has two extracellular Ig-like domains (FIG. 7). The gene for CARL is located between genes for epithelial V-like antigen 1 (ENSMUSG0000032092) and sodium channel beta-2 subunit (ENSMUSG0000037714) on mouse chromosome 9. CARL matched with BC050133 (gi29477100), which is deposited as "similar to AMICA". When the NCBI nr was searched for the nucleotide sequence of CARL using blastn, high homology to XM_194453 (gi38089807) in addition to BC050133 (gi29477100) was shown. XM_194453 (gi38089807) is a mutant of BC050133 (gi29477100), in which the first eleven amino acids are replaced with 37 amino acids, and an arginine at position 231 is replaced with glutamine. Moreover, according to the orthologue prediction in the mouse Ensembl, ENSG00000160593 deposited as "AMICA" was predicted to be a human orthologue of CARL. There are two types of ENSG00000160593 transcripts, and they (ENST00000292067 and ENST00000303475) are 5'-end splicing variants. A comparison between their deduced amino acid sequences showed that instead of the first 14 amino acids of ENST00000292067, four different amino acids were inserted in ENST00000303475. Homology between CARL and AMICA (ENST00000292067 and ENST00000303475) was 38.2% and 37.7% at the amino acid level, respectively. Since the human AMICA locus is located on chromosome 11 (11q23.3), a region homologous to mouse CARL on the human chromosome, human AMICA is thought to be human CARL, a human homologue for mouse CARL. Recently, human JAML (AJ515553) was reported as an adhesion molecule expressed in bone marrow-derived cells (Blood, 2003 (102), 3371-3378), but this molecule is a mutant lacking the 37 nucleotides from 560 to 596 bp of human CARL (ENST00000292067) and having this sequence inserted between 693 and 694 bp. Like human CARL, human JAML comprises of 394 amino acids, but the amino acid sequence of human JAML at position 94, and position 161 to 205 are completely different from human CARL.

Example 11

Figure 8:
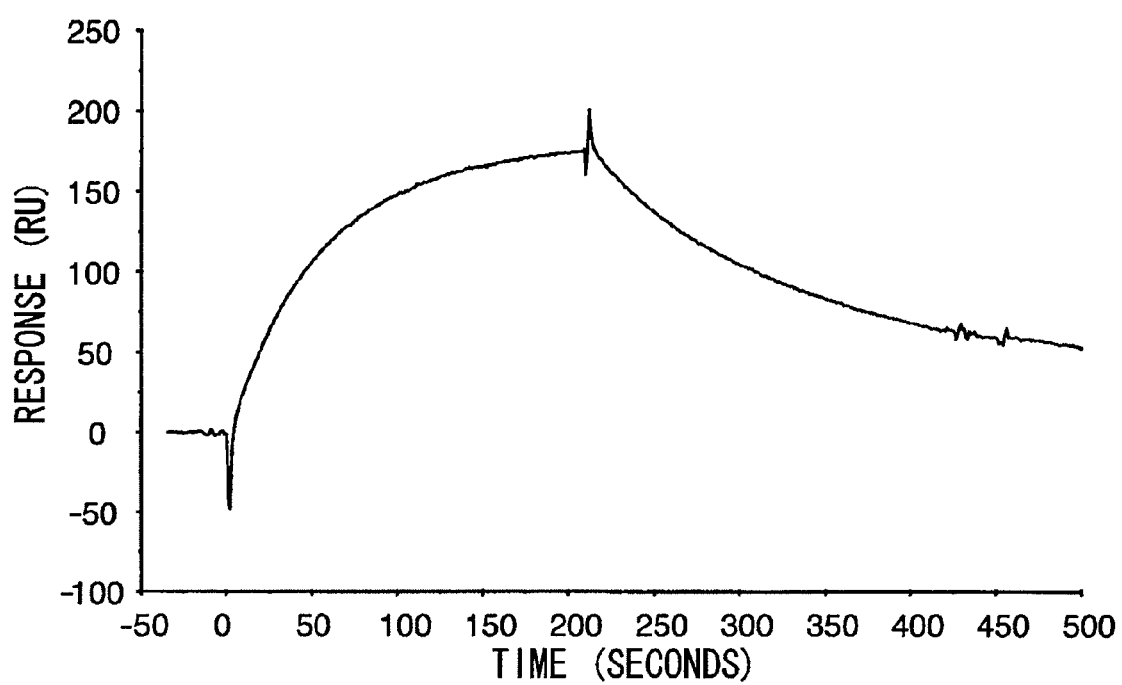
FIG. 8 is a graph showing the Kd value between CAR and CARL.

Protein-Protein Interaction Between CAR and the Extracellular Region of CARL, and their Dissociation Equilibrium Constant To examine the protein-protein interaction and affinity between CAR and the extracellular domain of CARL, the value of the dissociation equilibrium constant Kd was determined with a biosensor that uses the surface plasmon resonance phenomenon using BIAcore X (BIAcore), with the following procedure: first, anti-alkaline phosphatase antibodies (Seradyn) at 50 µg/ml were immobilized onto sensor chip CM5 (BIAcore) using the amino-coupling method. Then, a culture supernatant comprising CAR-AP chimeric protein or control AP chimeric protein diluted to 20 nM with HBS-EP buffer (BIAcore) was added to immobilize 500 RU of AP chimeric proteins onto the sensor chip. The protein-protein interactions were measured by adding culture supernatants comprising CARL-Fc chimeric proteins diluted to 20 nM, 6 nM, or 0.6 nM with HBS-EP buffer (BIAcore) at 20 µl/min for 210 seconds. From the binding rate constant and dissociation rate constant obtained using BIAevaluation software version 3.2 (BIAcore), the dissociation equilibrium constant between CAR and CARL was revealed to be 4.8 nM (FIG. 8).

Example 12

Figure 9:
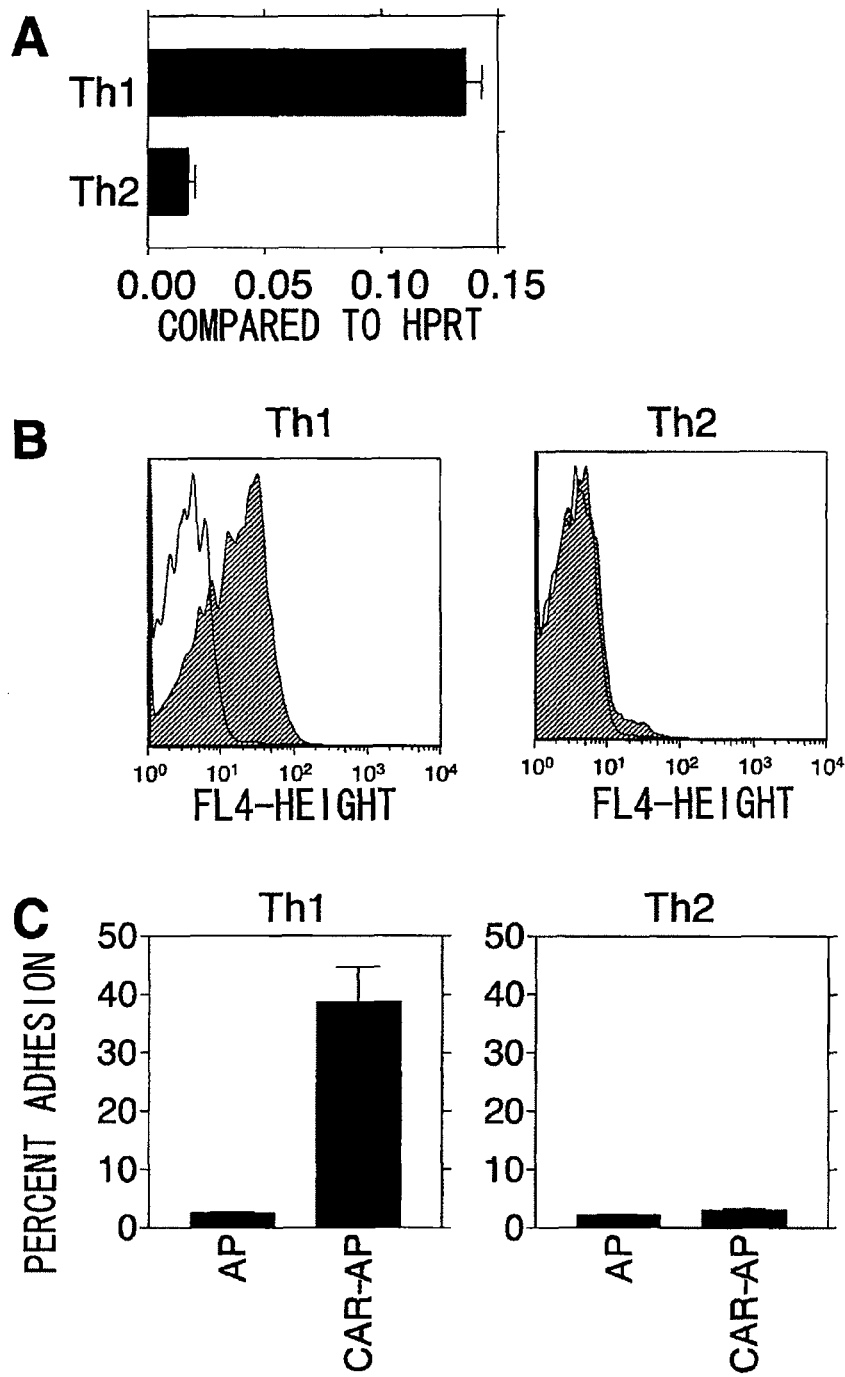
FIG. 9 shows that CAR selectively adheres to Th1 cells via binding with CARL, which is expressed selectively in Th1 cells.
Figure 10A:
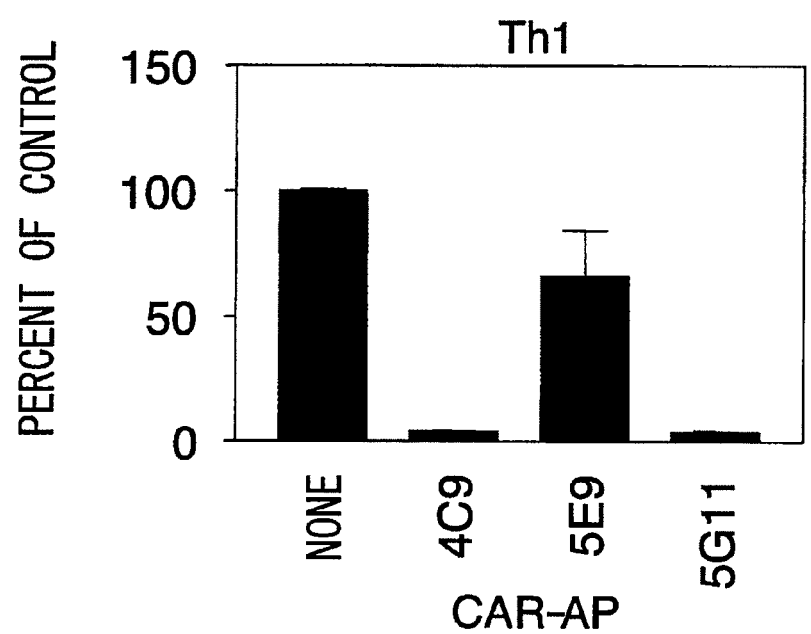
FIG. 10A is a graph showing the inhibition by anti-CAR antibodies of the cell adhesion of Th1 cells to CAR.

Selective Expression of CARL in Th1 Cells and Selective Adhesion of Th1 Cells to CAR Th1 and Th2 cells were prepared to investigate the expression of CARL in Th1 and Th2 cells. CD4-positive cells purified with MACS were added to plates onto which anti-CD3 antibodies at 1 µg/ml have been immobilized, and were then stimulated in the presence of 10 µg/ml anti-CD28 antibodies. The cells stimulated with anti-CD3 antibodies in the presence of 10 ng/ml IL-12 and 10 µg/ml anti-IL-4 antibodies (MP4-25D2; PharMingen) in the case of differentiation into Th1 cells, and in the presence of 15 ng/ml IL-4 and 15 µg/ml anti-IL-12 antibodies (24910.1; R & D Systems) in the case of differentiation into Th2 cells. After two days, the cells differentiated into Th1 were cultured in the presence of 20 ng/ml IL-2 and 10 ng/ml IL-12, while the cells differentiated into Th2 were cultured in the presence of 20 ng/ml IL-2 and 15 ng/ml IL-4. The cells were used in experiments seven to nine days after the stimulation. Cell differentiation into Th1 and Th2 was confirmed based on IFN-γ and IL-4 production, respectively. The expression of CARL and HPRT (control) mRNAs was investigated by real-time PCR using RNA obtained from these cells. The results revealed that CARL was selectively expressed in Th1 cells (FIG. 9A). When the cell surface binding activity of CAR-AP chimeric proteins was examined, a selective binding to Th1 cells was similarly observed (FIG. 9B). Furthermore, when the adhesion activity of Th1 and Th2 cells to CAR-AP chimeric proteins was examined, it was revealed that only Th1 cells selectively adhered to CAR, matching with the expression of CARL (FIG. 9C). Adhesion was inhibited by 4C9 and 5G11 (FIG. 10A).

Further, CARL expression was analyzed in cells other than CD4-positive T cells. Cells were prepared from the spleens and peripheral blood of C57BL/6 male mice and suspended in FACS buffer (PBS/1% FBS/1 mM EDTA) containing 5% mouse serum and 5% rat serum. An FcR blocking solution was added thereto, and incubation was carried out on ice for ten minutes. Then, fluorescently labeled anti-mCARL antibody was reacted on ice for 30 minutes with fluorescently labeled antibodies against various cell line markers, and measurements were carried out using FACScalibur.

Figure 10B:
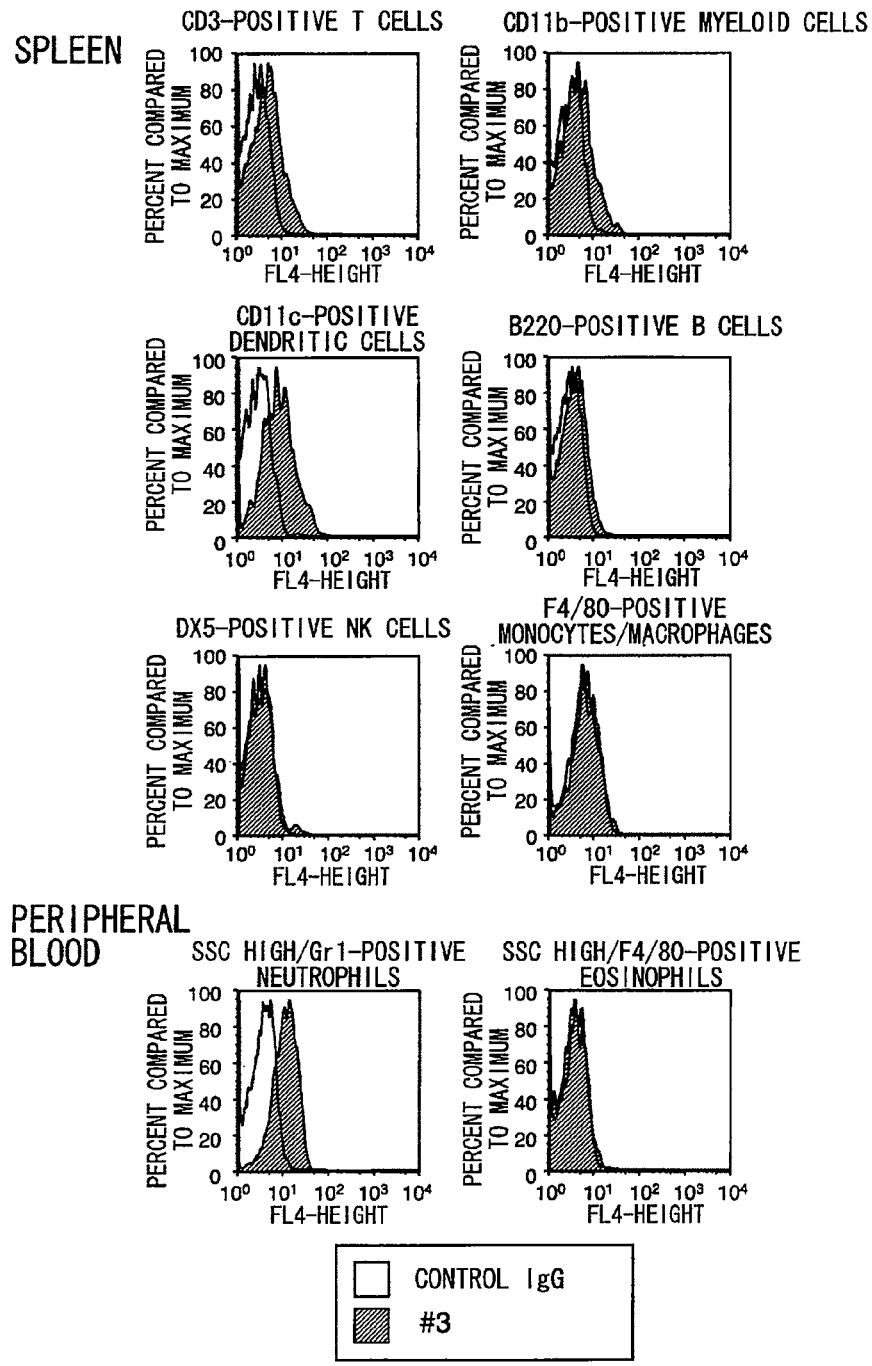
FIG. 10B shows the expression of CARL in cells other than CD4-positive T cells.

As a result, in the immune tissues of normal mice, CARL expression was detected in CD3-positive T cells, CD11b-positive myeloid cells, CD11c-positive dendritic cells, and B220-positive B cells prepared from the spleen, but not in DX5-positive NK cells and F4/80-positive monocytes/macrophages. Furthermore, the expression of CARL was detectable in SSC high/Gr1-positive neutrophils prepared from peripheral blood, but not in SSC high/F4/80-positive eosinophils (FIG. 10B).

Example 13

Preparation of Cells Expressing CARL Lacking Ig-Like Domains

Cells expressing mCARL lacking Ig-like domains were produced to determine the mCAR-binding region in CARL. Expression vectors were modified as described below. First, the modified vector pMX MCS2.2 IRES Puro was constructed by newly inserting a multi-cloning site (cgcggatc-ctaattaaggtttaaactgtcgacgaattcgcggccgccacgcgttcgcga; SEQ ID NO:19) and IRES/Puro between the BamHI and SalI of pMX (J. Biol. Chem., 2002, 277, 5583-5587), using the same method as described in Oncogene (2000) 19(27):3050-3058. Then, the modified vector pMX ssFLAG MCS2.2 IRES Puro was produced by inserting a signal sequence and FLAG tag between BamHI and SalI of pMX MCS2.2 IRES Puro.

The signal sequence of CARL was presumed to be the amino acids from position 1 to 20; the first Ig-like domain (domain 1) was presumed to be the amino acids from position 30 to 139; and the second Ig-like domain (domain 2) was presumed to be the amino acids from position 143 to 254 (SignalP, on the world wide web at cbs.dtu.dk/services/SignalP/; SMART, on the world wide web at smart.embl-heidelberg.de/). Thus, the full-length CARL indicates a protein comprising the amino acids from position 21 to 379; domain 1-lacking CARL indicates a protein comprising the amino acids from position 21 to 29 and from position 140 to 379; and domain 2-lacking CARL indicates a protein comprising the amino acids from position 21 to 139 and from position 255 to 379.

Figure 11:
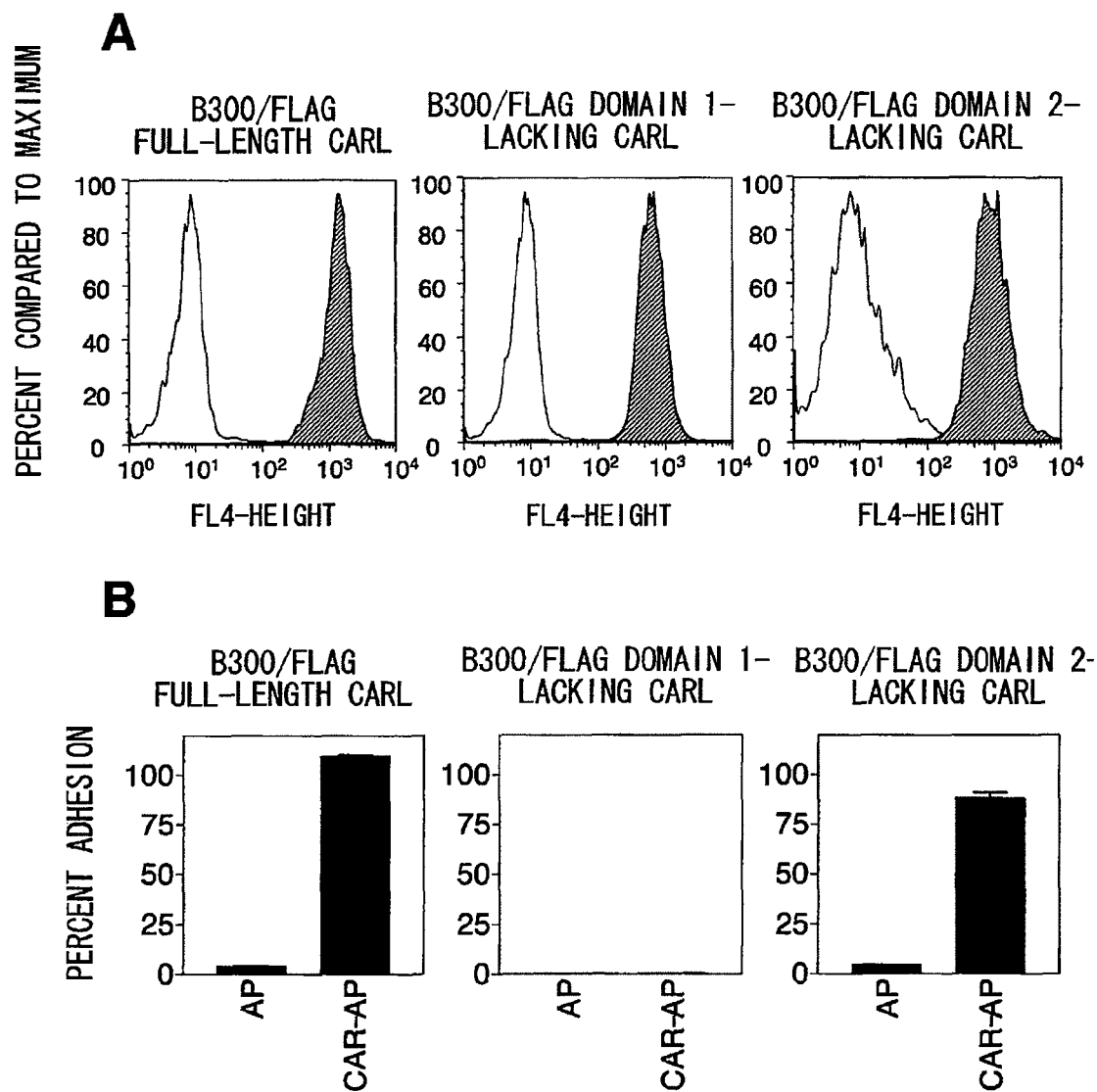
FIG. 11 shows that the region of CARL required for binding to CAR is the first Ig-like domain of CARL.

The full-length CARL and domain 1-lacking CARL were cloned by PCR amplification using the full-length CARL cDNA obtained in Example 9 as a template, and then inserting the obtained cDNA fragments into the expression vector pMX ssFLAG MCS2.2 IRES Puro. The domain 2-lacking CARL was cloned by amplifying a cDNA fragment by two-step PCR using primers comprising the nucleotide sequences corresponding to the amino acid sequence from position 134 to 139 and to the amino acid sequence from position 255 to 260 as well as the complementary sequences. The B300 cell line was infected with a recombinant retrovirus produced by the method described in Example 1 and expressing cells were obtained by selecting the gene-introduced cells with 5 µg/ml puromycin. The expression of CARLs lacking the Ig-like domains on the surface of cells was confirmed using anti-FLAG antibody (SIGMA) (FIG. 11A). The adhesion activity of the cells to CAR-AP chimeric proteins was examined by the method described in Example 4. B300 cells expressing full-length CARL and B300 cells expressing CARL lacking domain 2 adhered to CAR-AP chimeric proteins, while B300 cells expressing CARL lacking domain 1 did not (FIG. 11B). Thus, domain 1 of CARL was revealed to be essential for the binding between CAR and CARL.

Example 14

Figure 12:
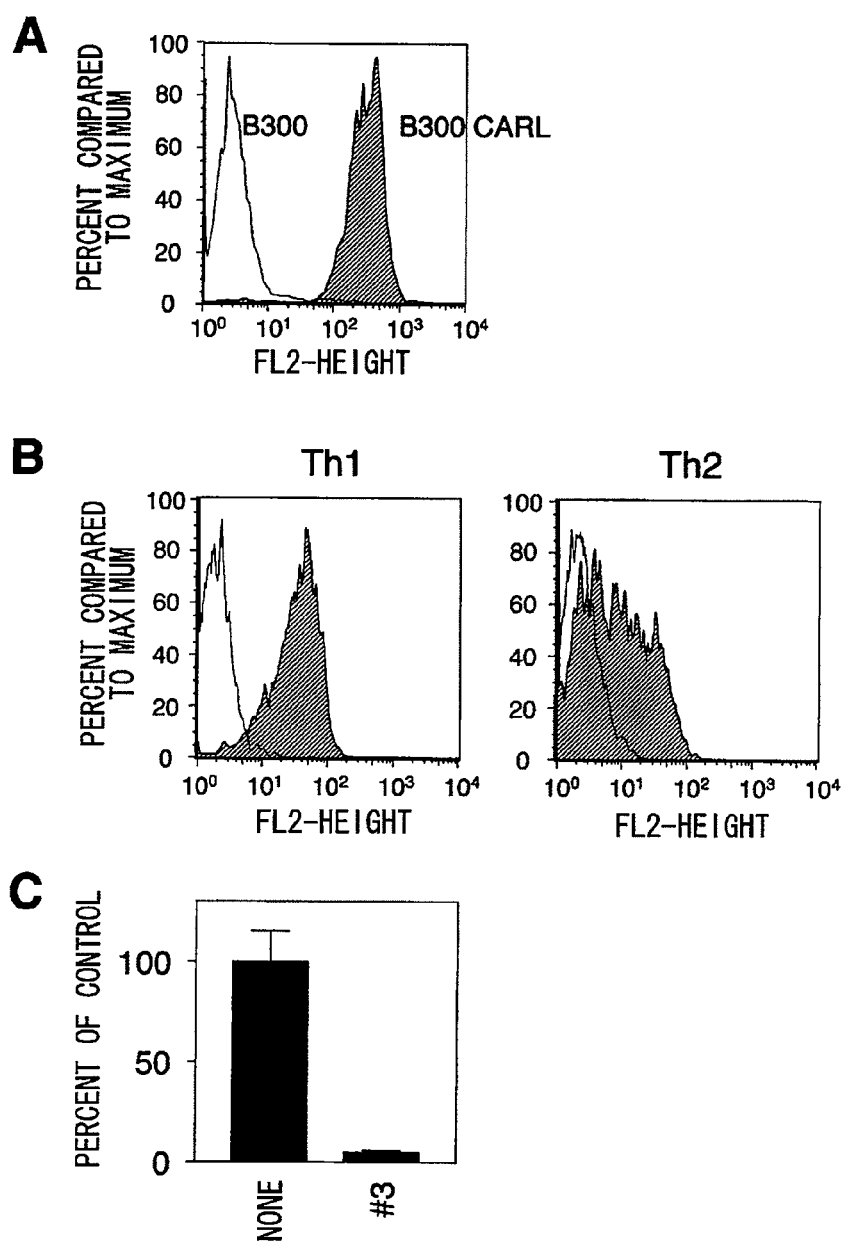
FIG. 12 shows the inhibition of cell adhesion by anti-CARL antibodies.

Preparation of Monoclonal Antibodies Against CARL, and Expression in Th1 Cells and Cell Adhesion Inhibition Activity Using Anti-CARL Antibodies Anti-CARL antibody #3 was obtained by the method described in Example 5, using as an immunization antigen the CARL-AP chimeric protein obtained in Example 9. Specificity was examined by FACS and the results showed that #3 antibody reacted with CARL-expressing B300 cells but not with the parental cell line B300 (FIG. 12A). When CARL expression in Th1 and Th2 cells prepared by the method described in Example 12 was examined using #3 antibody, CARL was strongly and selectively expressed in Th1 cells (FIG. 12B). Meanwhile, #3 antibody inhibited the adhesion of CAR-expressing B300 cells to CARL-AP proteins (FIG. 12C). When immunostaining was carried out using the cells obtained in Example 13, #3 antibody bound to CARL on the cell membrane of B300 cells expressing the full-length CARL and B300 cells expressing CARL lacking domain 2, but not to the CARL of B300 cells expressing CARL lacking domain 1. Thus #3 antibody, which has the activity of inhibiting binding, was revealed to recognize domain 1, which is required for the binding between CAR and CARL.

Example 15

Binding Between Human CAR and Human CARL

Cells expressing a full-length human CAR and cells expressing a full-length human CARL, as well as AP chimeric proteins with the extracellular region of human CAR and AP chimeric proteins with the extracellular region of human CARL were generated to verify that the phenomena observed in mice is similarly observed in humans. The expression vector used was pMX MCS2.2 IRES Puro, obtained in Example 13.

The full-length cDNAs for human CAR and CARL were cloned as follows: cDNAs synthesized from human whole brain (Clontech) were used as template. The primers used were designed as shown below, based on the sequences in GenBank™ (human CAR (NM_001338) and human CARL (AY138965)), and amplification was carried out by PCR.

```
                                        (SEQ ID NO: 11)
hCAR F1:    CGCGTCGACATGGCGCTCCTGCTGTGCTTCGTG (SEQ ID NO: 12)
hCAR R2:    GCGGGCGGCCGCCTATACTATAGACCCATCCTTGCT (SEQ ID NO: 13)
hCARL F1:   CGCGTCGACATGTTTTGCCCACTGAAACTCATC (SEQ ID NO: 14)
hCARL R2:   GCGGGCGGCCGCTCAAAAGGCTTGCTGTGTTTTGG
```

Each of the obtained cDNA fragments was inserted into the expression vector pMX MCS2.2 IRES Puro, and recombinant retroviruses were produced by the method described in Example 1. Expressing cells were obtained by selecting the gene-introduced B300 cell lines with 5 µg/ml puromycin. AP chimeric proteins with the extracellular domains of human CAR and CARL were generated by the method described in Example 3, using the following primers:

```
                                        (SEQ ID NO: 11)
hCAR F1:    CGCGTCGACATGGCGCTCCTGCTGTGCTTCGTG (SEQ ID NO: 15)
hCAR R1:    GCGGGCGGCCGCTTTATTTGAAGGAGGGACAACGTT (SEQ ID NO: 13)
hCARL F1:   CGCGTCGACATGTTTTGCCCACTGAAACTCATC (SEQ ID NO: 16)
hCARL R1:   GCGGGCGGCCGCATTACCACCCAAGACCAGAGGCCT
```

Figure 13:
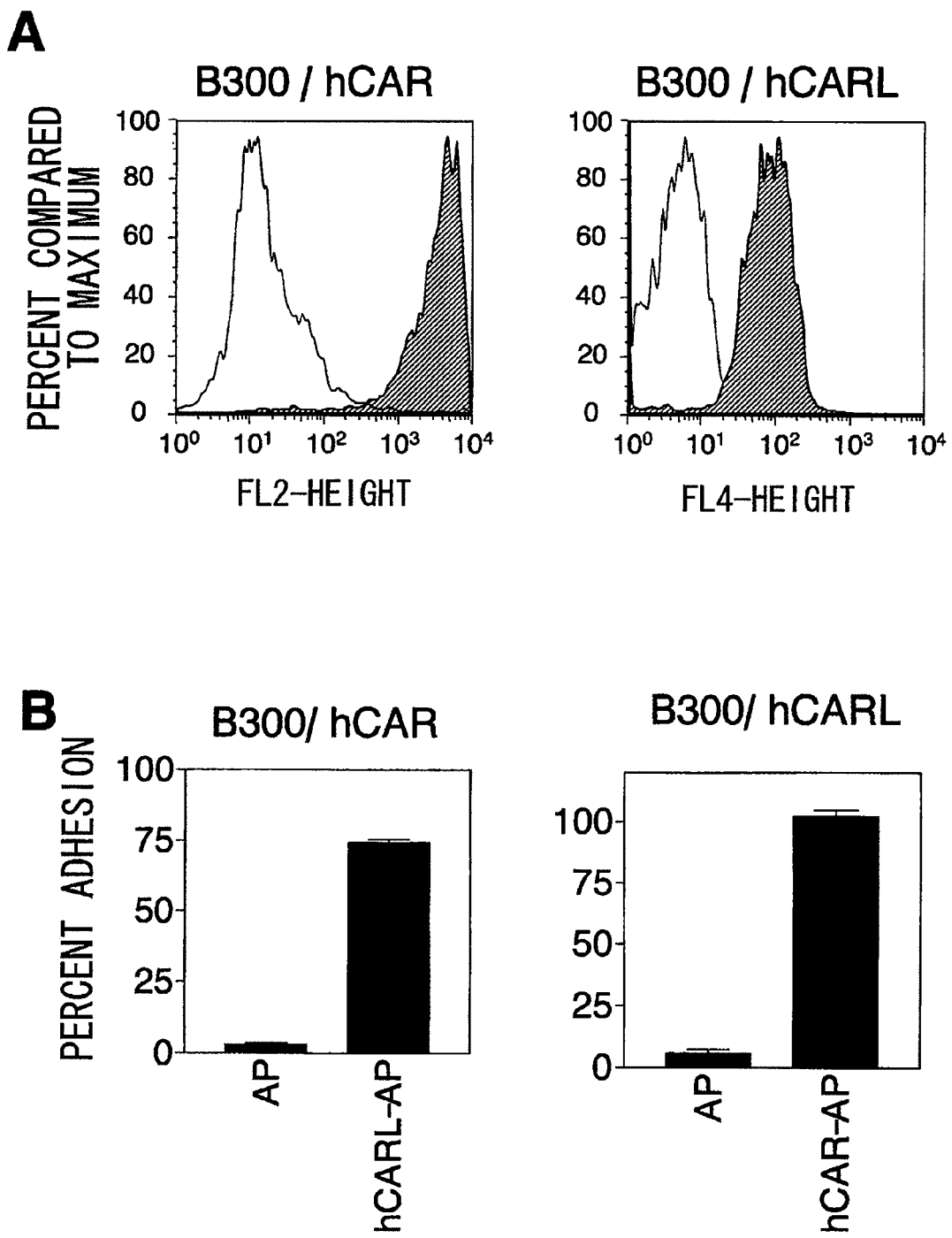
FIG. 13 shows that human CAR and human CARL bind to each other.

The expression of human CAR on the surface of human CAR-expressing B300 cells was confirmed using an anti-human CAR antibody (Upstate Biotechnology), while the expression of human CARL on the surface of human CARL-expressing B300 cells was confirmed using human CAR-AP chimeric proteins (FIG. 13A). When, the adhesion activity of human CAR-expressing B300 cells to human CARL-AP chimeric proteins was examined by the method described in Example 4, binding between human CAR and human CARL was detected. Likewise, when the adhesion activity of human CARL-expressing B300 cells to human CAR-AP chimeric proteins was examined, binding between human CAR bound to human CARL was detected (FIG. 13B).

Example 16

Figure 14:
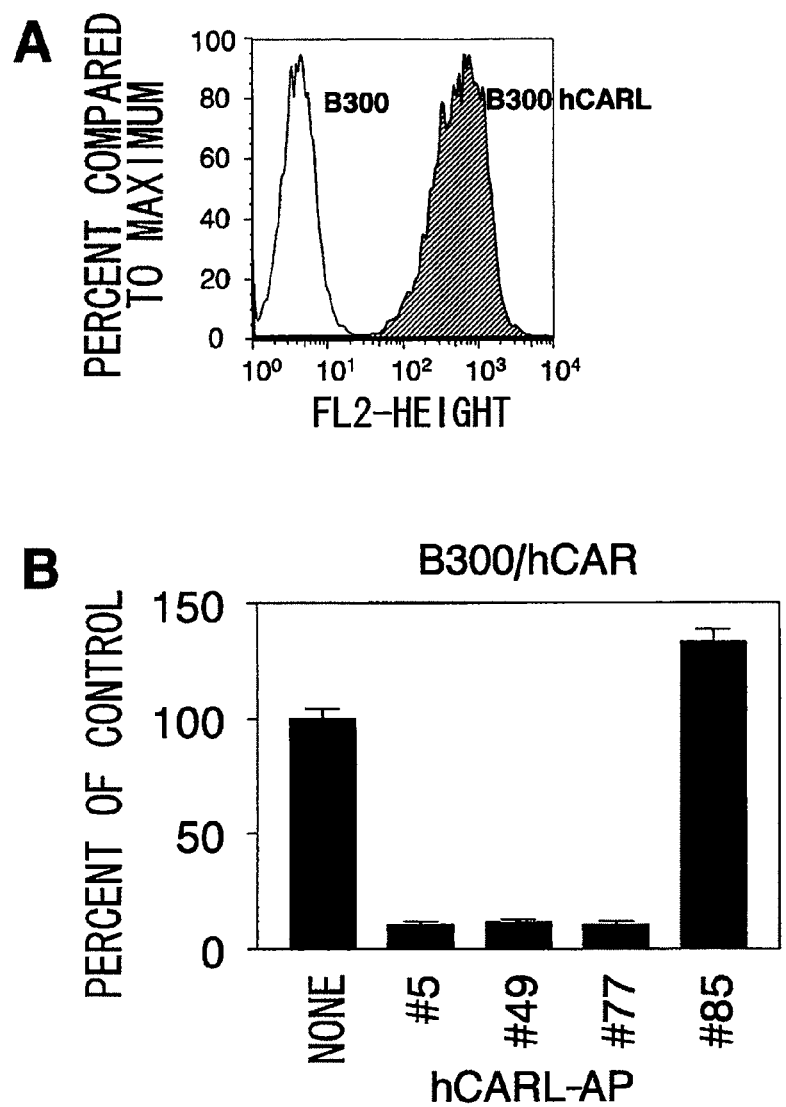
FIG. 14 shows the inhibition of cell adhesion by antibodies against human CARL.

Generation of Monoclonal Antibodies Against Human CARL and Cell Adhesion-Inhibiting Activity of Anti-Human CARL Antibodies Four types of mouse anti-human CARL antibodies (#5, #49, #77, and #85) were obtained by the method described in Example 5, using as immunization antigens the human CARL-AP chimeric proteins obtained in Example 15. Specificity was examined by FACS, and as a result, the culture supernatant of #5 reacted with B300 cells expressing human CARL, but not with the parental cell line B300 (FIG. 14A). Similar results were obtained with clones #49, #77, and #85. Of these antibodies, the culture supernatants of #5, #49, and #77 inhibited the adhesion of human CAR-expressing B300 cells to human CARL-AP chimeric proteins (FIG. 14B).

Example 17

Therapeutic Effect of Anti-CARL Antibody on Contact Dermatitis

Figure 15:
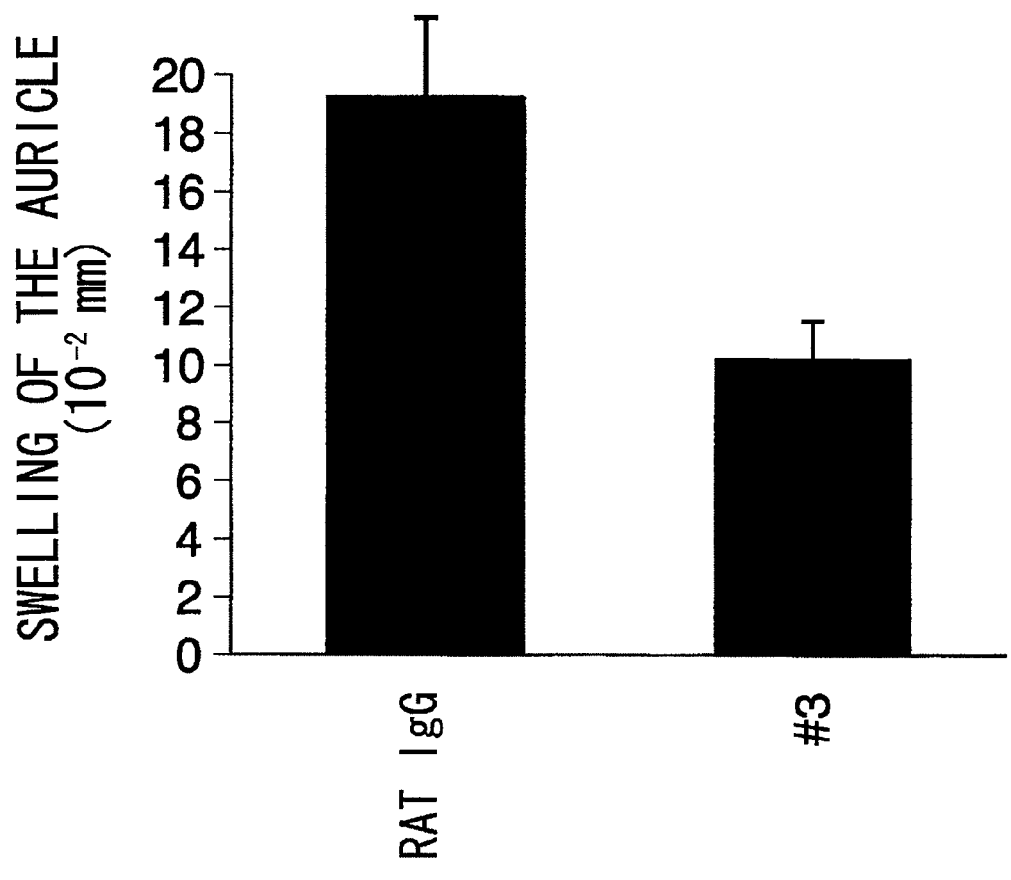
FIG. 15 is a graph showing the therapeutic effects of anti-CARL antibody on contact dermatitis.

Contact hypersensitivity (CHS) was induced in 6-week-old mice as follows: first, mice were sensitized five and four days before CHS induction by applying 25 µl of 0.4% dinitrofluorobenzene (WAKO) onto the abdomen of each mouse. Anti-CARL antibody #3 was administered at a dose of 500 µg per mouse from the caudal vein five days before and on the day of CHS induction. Then, CHS was induced by applying 20 µl of 0.4% dinitrofluorobenzene per mouse onto the ear auricles. The thickness of right and left auricles was measured 24 hours after induction. The swelling of auricles was suppressed by the antibody treatment (FIG. 15).

As shown in Example 12, CARL expression was observed in activated Th1 cells and neutrophils, and the anti-CARL antibody was thought to suppress CHS by suppressing the interaction between CARL and CAR.

INDUSTRIAL APPLICABILITY

The present invention provides methods for detecting Th1 cells. Th1 cells are CD4+ T lymphocytes, and when activated they secrete cytokines such as IL-2, IL-12, tumor necrosis factor (TNF) β, lymphotoxin (LT), and IFN-γ. Th1 cells are chiefly involved in cellular immunity. Th1 is thought to play a major role in the onset of organ-specific autoimmune diseases, comprising rheumatoid arthritis, Crohn's disease, type I diabetes, and multiple sclerosis. Moreover, selective imbalances or imbalanced activation of Th1 or Th2 cells is thought to be a cause of some chronic inflammatory or allergic diseases. On the other hand, the Th2 response dominates in diseases such as cancer, allergies (atopic disease and such), and parasite infections; however, it has been suggested that these diseases may be eased by inducing the Th1 response. Specifically, it has been reported that a shift to the Th1 phenotype increases the secretion of IFNα, IFN β and IFN γ, and IL-12, IL-18, and such, and strengthens host immunological defense against intracellular pathogens, such as viruses. Given this, the methods of the present invention for detecting Th1 cells can be used, for example, to diagnose or elucidate diseases in which a selective imbalance or imbalanced activation of Th1 or Th2 cells, or such, is involved. The methods can also be used to assess therapeutic effects on such diseases.

Furthermore, the present invention relates to methods of screening for inhibitors of the binding between CAR and CARL. Inhibitors of the binding between CAR and CARL comprise antibodies and inhibit the cell adhesion between Th1 cells expressing CARL and epithelial cells and endothelial cells expressing CAR. These inhibitors and compositions comprising these inhibitors are thus expected to suppress the adhesion of Th1 cells. With these inhibitors and compositions comprising the inhibitors, therapeutic effects on autoimmune diseases in which Th1 cells are involved are expected.

The present invention also provides antibodies that inhibit the binding between CAR and CARL. Like the substances described above, such antibodies are expected to suppress the adhesion of Th1 cells, to suppress cell adhesion in, for example, contact dermatitis, and to alleviate diseases. Moreover, since the binding between CAR and CARL is thought to be involved in the infiltration of Th1 cells, they are expected to be useful for elucidating the mechanism of cell infiltration.

The invention claimed is:

1. An isolated monoclonal antibody that specifically binds to a protein consisting of the amino acid sequence of SEQ ID NO:2, wherein the antibody binds to domain 1 (amino acids 27-136 of SEQ ID NO:2) and inhibits binding between the protein consisting of the amino acid sequence of SEQ ID NO:2 and a protein consisting of the amino acid sequence of SEQ ID NO:17.

2. An isolated human antibody that specifically binds to a protein consisting of the amino acid sequence of SEQ ID NO:2, wherein the antibody binds to domain 1 (amino acids 27-136 of SEQ ID NO:2) and inhibits binding between the protein consisting of the amino acid sequence of SEQ ID NO:2 and a protein consisting of the amino acid sequence of SEQ ID NO:17.

3. An isolated humanized antibody that specifically binds to a protein consisting of the amino acid sequence of SEQ ID NO:2, wherein the antibody binds to domain 1 (amino acids 27-136 of SEQ ID NO:2) and inhibits binding between the protein consisting of the amino acid sequence of SEQ ID NO:2 and a protein consisting of the amino acid sequence of SEQ ID NO:17.

4. An isolated chimeric antibody that specifically binds to a protein consisting of the amino acid sequence of SEQ ID NO:2, wherein the antibody binds to domain 1 (amino acids 27-136 of SEQ ID NO:2) and inhibits binding between the protein consisting of the amino acid sequence of SEQ ID NO:2 and a protein consisting of the amino acid sequence of SEQ ID NO:17.

5. An isolated single chain antibody that specifically binds to a protein consisting of the amino acid sequence of SEQ ID NO:2, wherein the antibody binds to domain 1 (amino acids 27-136 of SEQ ID NO:2) and inhibits binding between the protein consisting of the amino acid sequence of SEQ ID NO:2 and a protein consisting of the amino acid sequence of SEQ ID NO:17.

6. The antibody of claim 1, wherein the antibody is an antibody fragment selected from the group consisting of an Fab fragment, an Fab' fragment, an F(ab')2 fragment, and an Fv fragment.

7. A pharmaceutical composition comprising the antibody of claim 1 and a physiologically acceptable carrier.

8. A pharmaceutical composition comprising the antibody of claim 2 and a physiologically acceptable carrier.

9. A pharmaceutical composition comprising the antibody of claim 3 and a physiologically acceptable carrier.

10. A pharmaceutical composition comprising the antibody of claim 4 and a physiologically acceptable carrier.

11. A pharmaceutical composition comprising the antibody of claim 5 and a physiologically acceptable carrier.

12. A pharmaceutical composition comprising the antibody of claim 6 and a physiologically acceptable carrier.

* * * * *